US010779893B2

(12) United States Patent
Elliott et al.

(10) Patent No.: US 10,779,893 B2
(45) Date of Patent: Sep. 22, 2020

(54) SPINAL IMPLANT SYSTEM AND METHOD

(71) Applicant: Warsaw Orthopedic, Inc., Warsaw, IN (US)

(72) Inventors: John A. Elliott, Atoka, TN (US); Julien J. Prevost, Memphis, TN (US); Jerald L. Redmond, Germantown, TN (US); Mark R. Grizzard, Munford, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/163,645

(22) Filed: Oct. 18, 2018

(65) Prior Publication Data

US 2020/0121396 A1    Apr. 23, 2020

(51) Int. Cl.
| | | |
|---|---|---|
| *A61B 17/70* | (2006.01) | |
| *A61B 34/20* | (2016.01) | |
| *A61B 34/30* | (2016.01) | |
| *A61B 90/00* | (2016.01) | |
| *A61B 17/00* | (2006.01) | |

(52) U.S. Cl.
CPC ......... *A61B 34/20* (2016.02); *A61B 17/7074* (2013.01); *A61B 34/30* (2016.02); *A61B 90/361* (2016.02); *A61B 17/00234* (2013.01); *A61B 2017/00477* (2013.01); *A61B 2034/2051* (2016.02); *A61B 2034/2055* (2016.02); *A61B 2034/303* (2016.02); *A61B 2034/305* (2016.02)

(58) Field of Classification Search
CPC ...... A61B 17/7074–7092; A61B 34/20; A61B 2034/2048; A61B 2034/2051; A61B 2034/2055; A61B 17/70; A61B 2034/2046–2065
See application file for complete search history.

(56) References Cited

U.S. PATENT DOCUMENTS

| | | | | |
|---|---|---|---|---|
| 6,021,343 A | * | 2/2000 | Foley | A61B 17/16 600/417 |
| 9,198,698 B1 | * | 12/2015 | Doose | A61B 17/708 |
| 2005/0085714 A1 | * | 4/2005 | Foley | A61B 17/1735 600/424 |
| 2008/0243133 A1 | * | 10/2008 | Heinz | A61B 17/7082 606/104 |
| 2009/0264895 A1 | * | 10/2009 | Gasperut | A61B 17/7082 606/104 |
| 2010/0030283 A1 | * | 2/2010 | King | A61B 17/7037 606/86 A |
| 2012/0168587 A1 | * | 7/2012 | Karsak | A61B 17/1703 248/291.1 |
| 2012/0296171 A1 | * | 11/2012 | Lovell | A61B 17/0206 600/213 |

(Continued)

*Primary Examiner* — Eduardo C Robert
*Assistant Examiner* — Michelle C Eckman
(74) *Attorney, Agent, or Firm* — Sorell, Lenna & Schmidt, LLP

(57) ABSTRACT

A surgical instrument adaptor comprises a member including a first mating surface that is removably attachable with a surgical instrument and a second mating surface that is connectable with an actuator. An image guide is attachable with the member and oriented relative to a sensor to communicate a signal representative of a position of the surgical instrument. Systems, surgical instruments, spinal implants and methods are disclosed.

20 Claims, 26 Drawing Sheets

(56) References Cited

U.S. PATENT DOCUMENTS

| | | | |
|---|---|---|---|
| 2013/0096570 A1* | 4/2013 | Solar | A61B 17/00234 606/108 |
| 2013/0261609 A1* | 10/2013 | Dicorleto | A61B 17/1622 606/1 |
| 2013/0282019 A1* | 10/2013 | Bouliane | A61B 17/7082 606/104 |
| 2014/0031722 A1* | 1/2014 | Li | A61F 2/4609 600/587 |
| 2014/0100583 A1* | 4/2014 | Butler | A61B 17/7082 606/104 |
| 2014/0100616 A1* | 4/2014 | Shipp | A61B 17/7082 606/86 A |
| 2014/0107708 A1* | 4/2014 | Biedermann | A61B 17/7082 606/278 |
| 2014/0277212 A1* | 9/2014 | Dauster | A61B 17/7086 606/86 R |
| 2014/0316420 A1* | 10/2014 | Ballard | A61B 17/7002 606/102 |
| 2015/0066042 A1* | 3/2015 | Cummins | A61B 17/7037 606/104 |
| 2015/0066084 A1* | 3/2015 | Petit | A61B 17/7032 606/246 |
| 2015/0105833 A1* | 4/2015 | Simpson | A61B 5/06 606/86 R |
| 2015/0112397 A1* | 4/2015 | Petit | A61B 17/7076 606/86 A |
| 2015/0201987 A1* | 7/2015 | Lemoine | A61B 17/8891 606/104 |
| 2015/0297315 A1* | 10/2015 | Fowler | A61B 46/00 600/407 |
| 2015/0305786 A1* | 10/2015 | Wehrle | A61B 90/98 606/86 A |
| 2015/0359572 A1* | 12/2015 | Reimels | A61B 17/7082 606/104 |
| 2016/0038195 A1* | 2/2016 | Genovese | A61B 17/7082 606/79 |
| 2016/0354162 A1* | 12/2016 | Yen | A61B 34/20 |
| 2017/0000583 A1* | 1/2017 | Lechner | A61B 17/32070 |
| 2017/0209286 A1* | 7/2017 | Palmatier | A61F 2/4611 |
| 2017/0252074 A1* | 9/2017 | Semingson | A61B 17/7085 |
| 2017/0252114 A1* | 9/2017 | Crawford | A61B 17/17 |
| 2017/0319246 A1* | 11/2017 | Mladenov | A61B 17/7086 |
| 2017/0340367 A1* | 11/2017 | Beger | A61B 17/7002 |
| 2018/0014858 A1* | 1/2018 | Biester | A61B 17/7037 |
| 2018/0014862 A1* | 1/2018 | Raina | A61B 17/7037 |
| 2018/0042645 A1* | 2/2018 | Gunn | A61B 17/00234 |
| 2018/0042650 A1* | 2/2018 | Gao | A61B 17/7082 |
| 2018/0055545 A1* | 3/2018 | Biedermann | A61B 17/7083 |
| 2018/0055546 A1* | 3/2018 | Beger | A61B 34/20 |
| 2018/0185072 A1* | 7/2018 | Rubin | A61B 17/708 |
| 2018/0214190 A1* | 8/2018 | Erramilli | A61B 17/7082 |
| 2018/0221108 A1* | 8/2018 | Broers | A61B 34/20 |
| 2018/0279993 A1* | 10/2018 | Crawford | A61B 17/7082 |
| 2018/0280092 A1* | 10/2018 | Van Beek | A61B 90/39 |
| 2018/0289426 A1* | 10/2018 | Dace | A61B 34/20 |
| 2018/0296283 A1* | 10/2018 | Crawford | G06T 7/30 |
| 2018/0303522 A1* | 10/2018 | Wall | A61B 34/20 |
| 2018/0311051 A1* | 11/2018 | Donaldson | A61F 2/4611 |
| 2018/0344301 A1* | 12/2018 | Wehrli | A61B 17/00 |
| 2019/0000372 A1* | 1/2019 | Gullotti | A61B 17/7077 |
| 2019/0021800 A1* | 1/2019 | Crawford | A61B 34/20 |
| 2019/0025046 A1* | 1/2019 | Wu | G01B 11/08 |
| 2019/0029736 A1* | 1/2019 | Wall | A61B 34/20 |
| 2019/0029737 A1* | 1/2019 | Wall | A61B 17/7082 |
| 2019/0105116 A1* | 4/2019 | Johnson | A61B 34/32 |
| 2019/0117280 A1* | 4/2019 | Avidano | A61B 17/7086 |
| 2019/0125452 A1* | 5/2019 | Loke | A61B 34/20 |
| 2019/0209080 A1* | 7/2019 | Gullotti | A61B 5/1072 |
| 2019/0231408 A1* | 8/2019 | DiCorleto | A61B 17/1622 |
| 2019/0231435 A1* | 8/2019 | Zucker | A61B 17/70 |
| 2019/0254729 A1* | 8/2019 | Rohlfing | A61B 17/7001 |
| 2019/0254730 A1* | 8/2019 | Rohlfing | A61B 17/7082 |
| 2019/0262083 A1* | 8/2019 | Roger | A61B 17/1757 |
| 2019/0269467 A1* | 9/2019 | Forsyth | A61B 34/20 |
| 2019/0274765 A1* | 9/2019 | Crawford | A61B 17/7082 |

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument adaptor is provided. The surgical instrument adaptor comprises a member including a first mating surface that is removably attachable with a surgical instrument and a second mating surface that is connectable with an actuator. An image guide is attachable with the member and oriented relative to a sensor to communicate a signal representative of a position of the surgical instrument. In some embodiments, systems, surgical instruments, spinal implants and methods are disclosed.

In one embodiment, a surgical system is provided. The surgical system comprises a surgical instrument including a distal end and a proximal mating surface. An adaptor includes a first mating surface that is removably attachable with the proximal mating surface and a second mating surface. An actuator is connected with the second mating surface. An image guide is attached with the adaptor and oriented relative to a sensor to communicate a signal representative of a position of the surgical instrument.

In one embodiment, the surgical system comprises a surgical instrument including a distal end and a proximal mating surface. An adaptor includes a first mating surface that is removably attachable with the proximal mating surface and a second mating surface. An actuator is connected with the second mating surface. An image guide includes a tubular body that defines an axial cavity configured for disposal of the adaptor and an emitter oriented relative to a sensor to communicate a signal representative of a position of the surgical instrument. An alternative surgical instrument is removably attachable with the first mating surface.

BRIEF DESCRIPTION OF THE DRAWINGS

The present disclosure will become more readily apparent from the specific description accompanied by the following drawings, in which.

DETAILED DESCRIPTION

Figure 1:
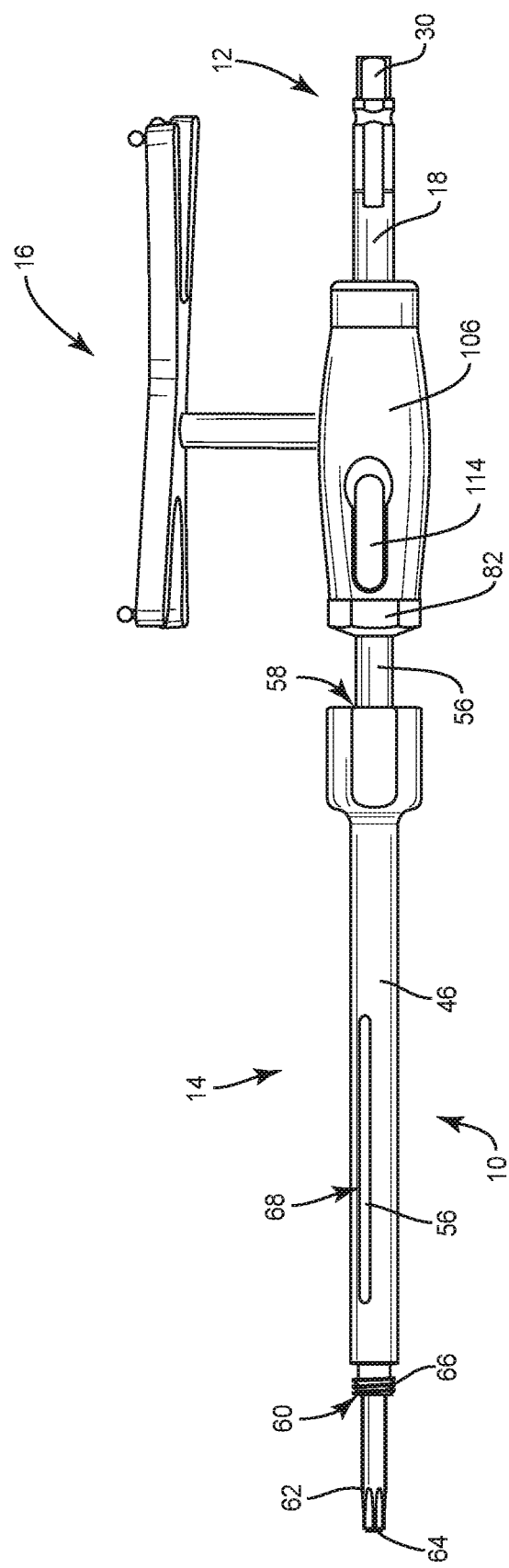
FIG. 1 is a side view of components of one embodiment of a surgical system in accordance with the principles of the present disclosure.
Figure 2:
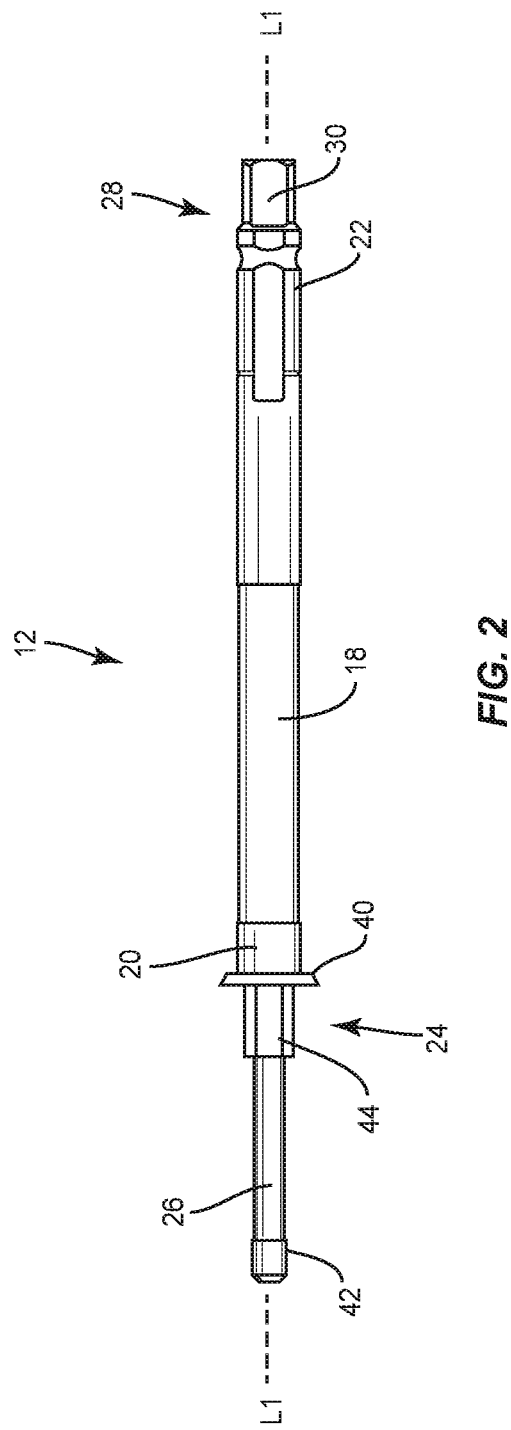
FIG. 2 is a side view of components of the surgical system shown in FIG. 1.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes an adaptor for use with surgical instrument having an image guide attachment that is used with navigation-guidewireless and robotic surgical procedures. In some embodiments, the present surgical system includes an adaptor for a surgically navigated instrument assembly. In some embodiments, the adaptor connects an image guide, an actuator such as a powered drill, handle or ratchet handle and a surgical instrument. In some embodiments, this configuration of present surgical system avoids an extended shaft length often associated with individual surgical instruments employed with navigation components. In some embodiments, this configuration of present surgical system decreases manufacturing costs by providing an adaptor usable with a plurality of surgical instruments employed with navigation components.

In some embodiments, the present surgical system includes a break-away adaptor for surgically navigated instruments. In some embodiments, the present surgical system includes an adaptor for use with one or more surgical instruments such that the adaptor is employed to streamline implant insertion with the adaptor maintaining assembly of the image guide, actuator and surgical instrument. In some embodiments, the present surgical system includes a surgically navigated instrument assembly having a removable adaptor and a mallet connectable with the assembly.

In some embodiments, the present surgical system includes an adaptor that is held to a surgical driver using no additional features. In some embodiments, the adaptor is connected to the surgical driver using image guide prongs. In some embodiments, the adaptor is connected to the surgical driver using a spring biased element. In some embodiments, the adaptor is connected to the surgical driver using a tension shaft. In some embodiments, the adaptor is configured of a length to reduce manufacturing cost of surgical instruments held to tight navigation tolerances. In some embodiments, the adaptor is configured of a length to reduce surgical instrument height to facilitate surgical techniques such as attachment to devices, for example, fenestrated screws connectable with bone filler device (BFD) attachments. In some embodiments, the present surgical system includes an adaptor that is employed with a bone screw that provides bi-cortical fixation to enhance fixation with vertebrae and reduce the risk of screw loosening when used with a biologic or agent, for example, bone cement (PMMA), and/or reduce the risk of biologic or agent leakage outside of a vertebral body.

In some embodiments, the present surgical system includes an adaptor configured to maintain connection of an image guide, actuator and surgical instrument to streamline surgical steps. In some embodiments, this configuration of present surgical system allows a quick connect/disconnect to surgical drivers. In some embodiments, the present surgical system includes a non-retaining adapter can be removed while navigating, which allows for connection to further attachments, such as, for example, a mallet insert.

In some embodiments, the surgical instrument comprises a screw driver. In some embodiments, the driver is configured for use with a spinal implant, such as, for example, a bone fastener or screw. The bone fastener may include open tulip head receivers and/or closed tulip head receivers. In some embodiments, the driver can be employed with a posted screw, a pedicle screw, a bolt, a bone screw for a lateral plate, a uni-axial screw (UAS), a fixed angle screw (FAS), a multi-axial screw (MAS), a side loading screw, a sagittal adjusting screw (SAS), a transverse sagittal adjusting screw (TSAS), an awl tip (ATS) or a sacral bone screw.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-7A, there are illustrated components of a surgical system, such as, for example, a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Surgical system 10 includes an adaptor 12 and a surgical instrument, such as, for example, a driver 14 that is removably attachable with adaptor 12. Surgical system 10 includes an image guide, such as, for example, a navigation component 16 that is removably attachable with adaptor 12 and/or driver 14, as discussed herein. Adaptor 12 includes a member, such as, for example, a shaft 18 extending along a longitudinal axis L1 between an end 20 and an opposite end 22. An end portion 24 of adaptor 12 extends from end 20 and includes a mating surface 26 configured for engagement with driver 14 to couple adaptor 12 to driver 14, as discussed herein. An end portion 28 of adaptor 12 extends from end 22 and includes a mating surface 30. In some embodiments, mating surface 30 includes one or a plurality of mating surfaces that define a drive portion configured for engagement with an actuator, as described herein, to rotate adaptor 12 and a portion of driver 14 about axis L1, as discussed herein. In some embodiments, the drive portion may include a square, triangular, polygonal, star or hexalobe cross sectional configuration configured engage a correspondingly shaped portion of the actuator. In some embodiments, end portions 24, 28 are separate and attachable with shaft 18. In some embodiments, end portions 24, 28 are monolithically formed with shaft 18. In some embodiments, shaft 18 may have various cross section configurations, such as, for example, circular, oval, oblong, triangular, rectangular, square, polygonal, irregular, uniform, non-uniform, variable, tubular and/or tapered. In some embodiments, the surgical instrument adaptor, as described herein, can be employed and/or attachable with various surgical instruments. See, for example, the embodiments and disclosure of surgical instruments, spinal implant systems and methods shown and described in commonly owned and assigned U.S. patent application Ser. No. 16/163,666 filed Oct. 18, 2018; and U.S. patent application Ser. No. 16/163,688 filed Oct. 18, 2018, the entire contents of each of these disclosures being incorporated herein by reference.

In some embodiments, adaptor 12 has a solid configuration that is free of any cavities or openings. In some embodiments, adaptor 12 is cannulated and includes an inner surface 32 defining a passageway 34 that extends continuously along the entire length of adaptor 12. End portion 24 includes an opening 36 that is in communication with passageway 34 and end portion 28 includes an opening 38 that is in communication with passageway 34 and coaxial with opening 36 such that a guide member, such as, for example, a guide wire can be inserted into passageway 34 through opening 38 and exit passageway 34 through opening 36. In some embodiments, passageway 34 may be disposed at alternate orientations, relative to axis L1, such as, for example, coaxial, parallel, transverse, perpendicular and/or other angular orientations such as acute or obtuse, co-axial and/or may be offset or staggered.

End portion 24 incudes a circumferential flange 40 positioned adjacent to end 20, a prong 42 that includes mating surface 26 and a section 44 positioned between flange 40 and prong 42. In some embodiments, shaft 18, flange 40, prong 42 and/or section 44 may have various cross section configurations, such as, for example, circular, oval, oblong, triangular, rectangular, square, polygonal, irregular, uniform, non-uniform, variable, tubular and/or tapered.

Driver 14 includes a tubular sleeve 46. Sleeve 46 extends along a longitudinal axis L2 between a proximal end 48 and a distal end 50. In some embodiments, sleeve 46 may have various configurations including, for example, round, oval, polygonal, irregular, consistent, variable, uniform and non-uniform. Sleeve 46 includes an inner surface 52 defining a cavity 54 configured for disposal of a shaft 56 of driver 14, as discussed herein. End 48 includes an opening 58 that is in communication with cavity 54 and end 50 includes an opening 60 that is in communication with cavity 54 such that an end 62 of shaft 54 can be inserted into cavity 54 through opening 58. Shaft 56 can be translated relative to sleeve 46 within cavity 54, in the direction shown by arrow D in FIG. 4, such that end 62 extends through opening 60, as shown in FIGS. 1, 3, 4 and 5. In some embodiments, shaft 56 is configured to translate relative to sleeve 46 within cavity 54 in opposite directions along axis L2. In some embodiments, shaft 56 is configured to rotate relative to sleeve 46 within cavity 54 in opposite directions about axis L2.

Figure 3:
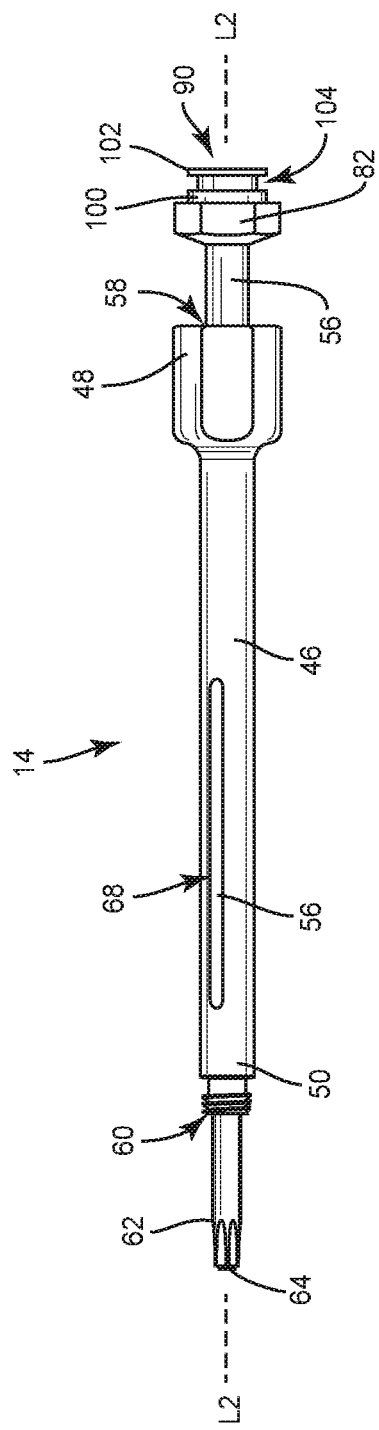
FIG. 3 is a side view of components of the surgical system shown in FIG. 1.
Figure 4:
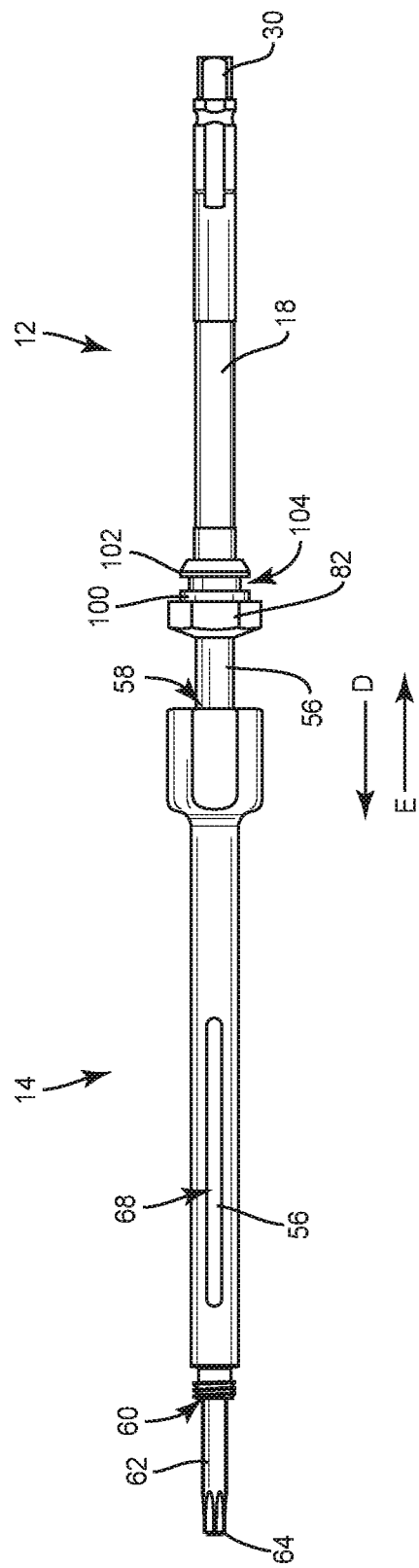
FIG. 4 is a side view of components of the surgical system shown in FIG. 1.

End 62 includes a tip 64 defining a drive bit. In some embodiments, tip 64 may include a square, triangular, polygonal, star or hexalobe cross sectional configuration configured engage a correspondingly shaped socket of a bone screw, such as for example, a socket in a shank of the bone screw. In some embodiments, the bone screw includes a receiver that is rotatable and/or pivotable relative to the shank of the bone screw and end 50 includes a threaded outer surface 66 configured to engage one or more threaded inner surfaces of the receiver to couple the receiver to end 50 while tip 64 is positioned within the socket of the shank of the bone screw. This configuration prevents the receiver of the bone screw from pivoting relative to the shank of the bone screw as the shank is rotated relative to the receiver about axis L2 by shaft 56. In some embodiments, sleeve 46 includes a window 68 that extends through surface 52 and an opposite outer surface of sleeve 46. A portion of shaft 56 is viewable through window 68, as shown in FIGS. 1, 3 and 4 to allow visualization of shaft 56 as shaft 56 translates relative to sleeve 46 along axis L2 and/or rotates relative to sleeve 46 about axis L2.

Shaft 56 includes an end 70 opposite end 62, End 70 includes a circumferential lip 72 that extends outwardly from an outer surface 74 of shaft 56. In some embodiments, lip 72 is configured to directly engage a surface 76 of sleeve 46 to prevent shaft 56 from translating relative to sleeve 46 along axis L2, in the direction shown by arrow D in FIG. 4, In some embodiments, end 62 includes a surface 78 that directly engages a surface 80 of end 50 when lip 72 engages surface 76 of sleeve 46 to prevent shaft 56 from translating relative to sleeve 46 along axis L2, in the direction shown by arrow D in FIG. 4, In some embodiments, lip 72, surface 76, surface 78 and/or surface 80 may be disposed at alternate orientations, relative to axis L2, such as, for example, transverse, perpendicular and/or other angular orientations such as acute or obtuse, and/or may be offset or staggered.

End 70 includes a hub 82 opposite tip 64 that is spaced apart from lip 72 along axis L2. In some embodiments, shaft 56 has a solid configuration that is free of any cavities or openings. In some embodiments, shaft 56 is cannulated and includes an inner surface 84 that defines an axial channel 86 extending the entire length of shaft 56. End 62 includes an opening 88 that is in communication with channel 86 and end 70 includes an opening 90 that is in communication with channel 86 such that a guide member, such as, for example, a guide wire can be inserted into channel 86 through opening 90 and be translated relative to shaft 56 within channel 86 along axis L2 such that the guide wire extends through opening 88. In some embodiments, hub 82 is spaced apart from lip 72 such that hub 82 directly engages sleeve 46 when lip 72 engages surface 76 and/or when surface 78 engages surface 80. In some embodiments, hub 82 is spaced apart from lip 72 such that hub 82 is spaced apart from sleeve 46 when lip 72 engages surface 76 and/or when surface 78 engages surface 80.

Figure 5:
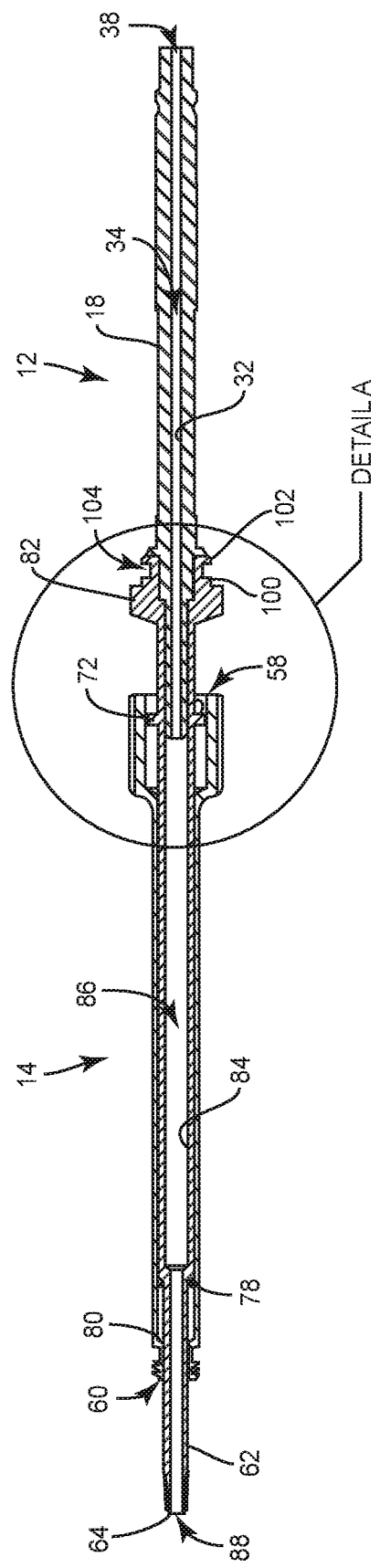
FIG. 5 is a side, cross section view of the components shown in FIG. 4.
Figure 6:
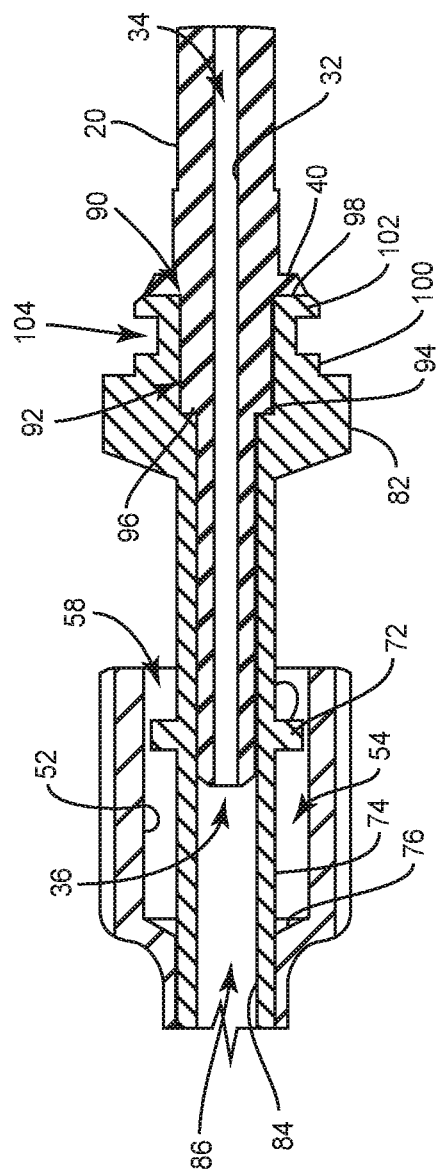
FIG. 6 is an enlarged view of detail A shown in FIG. 5.

Hub 82 includes an aperture 92 defined by surface 84 and a surface 94 that extends transverse to axis L2. Aperture 92 is in communication with channel 86 and opening 90 and is configured for disposal of section 44. Adaptor 12 is coupled to driver 14 by aligning axis L1 with axis L2 such that axis L1 is coaxial with axis L2 and inserting prong 42 into opening 90. Adaptor 12 is translated relative to shaft 56 along axes L1, L2, in the direction shown by arrow D in FIG. 4, such that a tip of prong 42 is positioned between hub 82 and tip 62, a surface 96 of section 44 directly engages surface 94, and flange 40 directly engages an end surface 98 of hub 82, as shown in FIGS. 5 and 6.

In some embodiments, adaptor 12 is connected to driver 14 such that adaptor 12 is fixed relative to shaft 56 such that rotation of adaptor 12 relative to sleeve 44 about axes L1, L2 also rotates shaft 56 relative to sleeve 46 about axes L1, L2. For example, in some embodiments, section 44 has a polygonal cross sectional configuration, such as, for example, a hexagonal cross sectional configuration and aperture 92 has a polygonal cross sectional configuration, such as, for example, a hexagonal cross sectional configuration that corresponds to the cross sectional configuration of section 44 such that an outer surface of section 44 directly engages surface 84 within aperture 92 to prevent adaptor 12 from rotating relative to shaft 56.

In some embodiments, adaptor 12 is configured to translate relative to shaft 56 in opposite directions along axis L2 such that adaptor 12 can be removed from driver 14 by translating adaptor 12 relative to shaft 56 along axes L1, L2, in the direction shown by arrow E in FIG. 4, until flange 40 is spaced apart from surface 98, section 44 is removed from aperture 92, and prong 42 is removed from channel 86. In some embodiments, adaptor 12 is configured to be reattached with driver 14 after adaptor 12 is removed from driver 14, as discussed herein.

Figure 7:
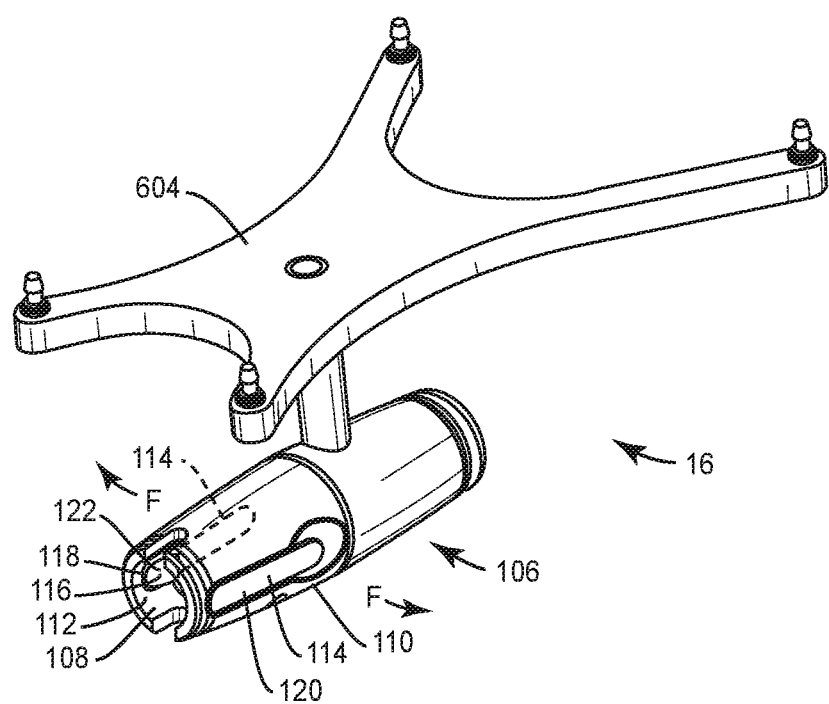
FIG. 7 is a perspective view of components of the surgical system shown in FIG. 1.

Hub 82 is configured to connect driver 14 with navigation component 16, as discussed herein. Hub 82 includes a flange 100 and a flange 102 that is spaced apart from flange 100. Hub 82 includes a recess 104 between flanges 100, 102. Navigation component 16 includes a collar 106 having an inner surface 108 and an outer surface 110. Surface 108 defines a passageway 112. Surface 108 is configured for releasable engagement with hub 82. Passageway 102 is configured to receive shaft 18 and a portion of hub 82. Surface 108 defines a lock, such as, for example, at least one resilient prong or tab 114. In one embodiment, collar 106 includes a plurality of tabs 114, as shown in FIG. 7. Each tab 114 includes an inner surface 116 that defines a cutout 118 and an outer surface 120. Each cutout 118 includes raised portions 122 that define edges of cutout 118. Cutout 118 is configured to receive flange 102. In its initial position, surface 120 is aligned with surface 110 of collar 106.

Navigation component 16 is connected with adaptor 12 and driver 14, as discussed herein. To connect navigation component 16 with adaptor 12 and driver 14, collar 106 is translated over shaft 18, in the direction shown by arrow D in FIG. 4, such that flange 40 and/or flange 102 engages portions 122 and applies a force to tabs 114 to move tabs 114 outwardly, in the direction shown by arrows F in FIG. 7, such that surface 120 is deflected from surface 110. As flange 40 and/or flange 102 translate over portions 122, flange 40 and/or flange 102 move into cutouts 118 allowing tabs 114 to move back to their initial position. In some embodiments, navigation component 16 is configured for removable engagement with adaptor 12 and driver 14. In some embodiments, navigation component 16 may be integrally formed with adaptor 12 and/or driver 14. In one embodiment, flange 100 is configured to engage collar 106 to reduce vibrations resulting from the torque of an actuator. In some embodiments, adaptor 12 and driver 14 do not include any retention features and instead rely on the lock defined by tabs 114 to maintain the connection between adaptor 12 and driver 14. That is, adaptor 12 is prevented from translating relative to shaft 56 along axes L1, L2 when navigation component 16 is connected with adaptor 12 and driver 14, as discussed herein.

Figure 7A:
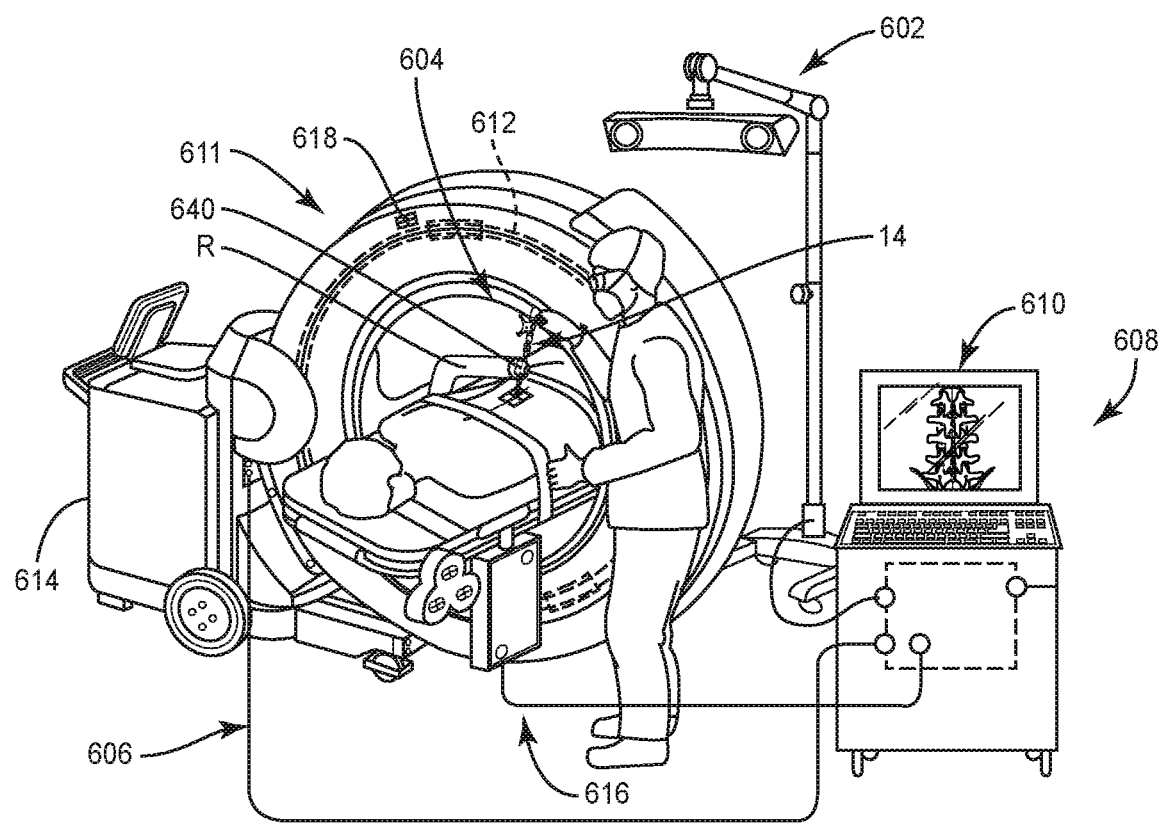
FIG. 7A is a perspective view of components of one embodiment of a surgical system in accordance with the principles of the present disclosure.

Driver 14 is configured for disposal adjacent a surgical site such that navigation component 16 is oriented relative to a sensor array 602 to facilitate communication between navigation component 16 and sensor array 602 during a surgical procedure, as shown in FIG. 7A. Navigation component 16 is configured to generate a signal representative of a position of a bone fastener (not shown) relative to driver 14 and/or tissue. In some embodiments, the image guide may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Navigation component 16 includes an emitter array 604, as shown in FIG. 7. Emitter array 604 is configured for generating a signal to sensor array 602 of a surgical navigation system 606, as shown in FIG. 7A. In some embodiments, the signal generated by emitter array 604 represents a position of a bone fastener relative to driver 14 and relative to tissue, such as, for example, bone. In some embodiments, the signal generated by emitter array 604 represents a three dimensional position of a bone fastener relative to tissue. In some embodiments, emitter array 604 includes a reflectance array and/or is configured to reflect a signal to sensor array 602.

In some embodiments, sensor array 602 receives signals from emitter array 604 to provide a three-dimensional spatial position and/or a trajectory of a bone fastener relative to driver 14 and/or tissue. Emitter array 604 communicates with a processor of a computer 608 of navigation system 606 to generate data for display of an image on a monitor 610. In some embodiments, sensor array 602 receives signals from emitter array 604 to provide a visual representation of a position of a bone fastener relative to driver 14 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 606 is configured for acquiring and displaying medical imaging, such as, for example, x-ray images appropriate for a given surgical procedure. In some embodiments, pre-acquired images of a patient are collected. In some embodiments, surgical navigation system 606 can include an O-arm® imaging device 611 sold by Medtronic Navigation, Inc. having a place of business in Louisville, Colo., USA. Imaging device 611 may have a generally annular gantry housing that encloses an image capturing portion 612.

In some embodiments, navigation system 606 comprises an image capturing portion 614 that may include an x-ray source or emission portion and an x-ray receiving or image receiving portion located generally or as practically possible 180 degrees from each other and mounted on a rotor (not shown) relative to a track of image capturing portion 614. Image capturing portion 614 can be operable to rotate 360 degrees during image acquisition. Image capturing portion 614 may rotate around a central point or axis, allowing image data of the patient to be acquired from multiple directions or in multiple planes. Surgical navigation system 606 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 606 can include C-arm fluoroscopic imaging systems, which can generate three-dimensional views of a patient. The position of image capturing portion 614 can be precisely known relative to any other portion of an imaging device of navigation system 606. In some embodiments, a precise knowledge of the position of image capturing portion 614 can be used in conjunction with a tracking system 616 to determine the position of image capturing portion 614 and the image data relative to the patient.

Tracking system 616 can include various portions that are associated or included with surgical navigation system 606. In some embodiments, tracking system 616 can also include a plurality of types of tracking systems, such as, for example, an optical tracking system that includes an optical localizer, such as, for example, sensor array 602 and/or an EM tracking system that can include an EM localizer. Various tracking devices can be tracked with tracking system 616 and the information can be used by surgical navigation system 606 to allow for a display of a position of an item, such as, for example, a patient tracking device, an imaging device tracking device 618, and an instrument tracking device, such as, for example, emitter array 604, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted a computer 614 where they may be forwarded to computer 608. Image transfer may be performed over a standard video connection or a digital link including wired and wireless. Computer 608 provides the ability to display, via monitor 610, as well as save, digitally manipulate, or print a hard copy of the received images. In some embodiments, images may also be displayed to the surgeon through a heads-up display.

In some embodiments, surgical navigation system 606 provides for real-time tracking of the position of a bone fastener relative to driver 14 and/or tissue can be tracked. Sensor array 602 is located in such a manner to provide a clear line of sight with emitter array 604, as described herein. In some embodiments, fiducial markers of emitter array 604 communicate with sensor array 602 via infrared technology. Sensor array 602 is coupled to computer 608, which may be programmed with software modules that analyze signals transmitted by sensor array 602 to determine the position of each object in a detector space.

In some embodiments, driver 14 is configured for use with a guide member, such as, for example, an end effector 640 of a robotic arm R. End effector 640 defines a channel configured for passage of a bone fastener and disposal of driver 14. Robotic arm R includes position sensors (not shown), similar to those referenced herein, which measure, sample, capture and/or identify positional data points of end effector 640 in three dimensional space for a guide-wireless insertion of bone fasteners with selected vertebral levels. In some embodiments, the position sensors of robotic arm R are employed in connection with surgical navigation system 606 to measure, sample, capture and/or identify positional data points of end effector 640 in connection with surgical treatment, as described herein. The position sensors are mounted with robotic arm R and calibrated to measure positional data points of end effector 640 in three dimensional space, which are communicated to computer 608.

In assembly, operation and use, a motorized and/or manual actuator is engaged with mating surface 30 to connect the actuator to adaptor 12. The actuator can be connected with adaptor 12 either before driver 14 or after, depending on a particular surgical procedure. In some embodiments, the actuator may be pneumatic, hydraulic and/or include a handle for hand rotation.

Access to the surgical site is obtained and the particular surgical procedure is performed. The components of surgical system 10, including adaptor 12, driver 14 and navigation component 16 are employed to augment the surgical treatment. For example, a bone fastener may be inserted into bone or other tissue with driver 14, for example via clockwise or counterclockwise rotation. The bone fastener may be delivered, introduced, inserted and/or removed from the bone or other tissue of vertebrae with driver 14. Upon completion of a surgical procedure, driver 14 may be disengaged from the bone fastener, and the non-implanted components, including adaptor 12, driver 14 and navigation component 16 may be removed from the surgical site and the incision closed.

In one embodiment, surgical system 10 is disassembled, as described herein, to facilitate cleaning of one or all of the components. Surgical system 10 may be re-assembled for use in a surgical procedure.

Surgical system 10 can include one or a plurality of bone fasteners such as those described herein and/or fixation elements, which may be employed with a single vertebral level or a plurality of vertebral levels. In some embodiments, the bone fasteners may be engaged with vertebrae in various orientations, such as, for example, series, parallel, offset, staggered and/or alternate vertebral levels. In some embodiments, the bone fasteners and/or fixation elements may include one or a plurality of multi-axial screws, sagittal angulation screws, pedicle screws, mono-axial screws, uniplanar screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, surgical system 10 may comprise various instruments including the configuration of the present disclosure, such as, for example, inserters, extenders, reducers, spreaders, distracters, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10, In some embodiments, the agent may include bone growth promoting material, such as, for example, bone graft to enhance fixation of the fixation elements with vertebrae. The components of surgical system 10 can be made of radiolucent materials such as polymers, Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration.

Figure 8:
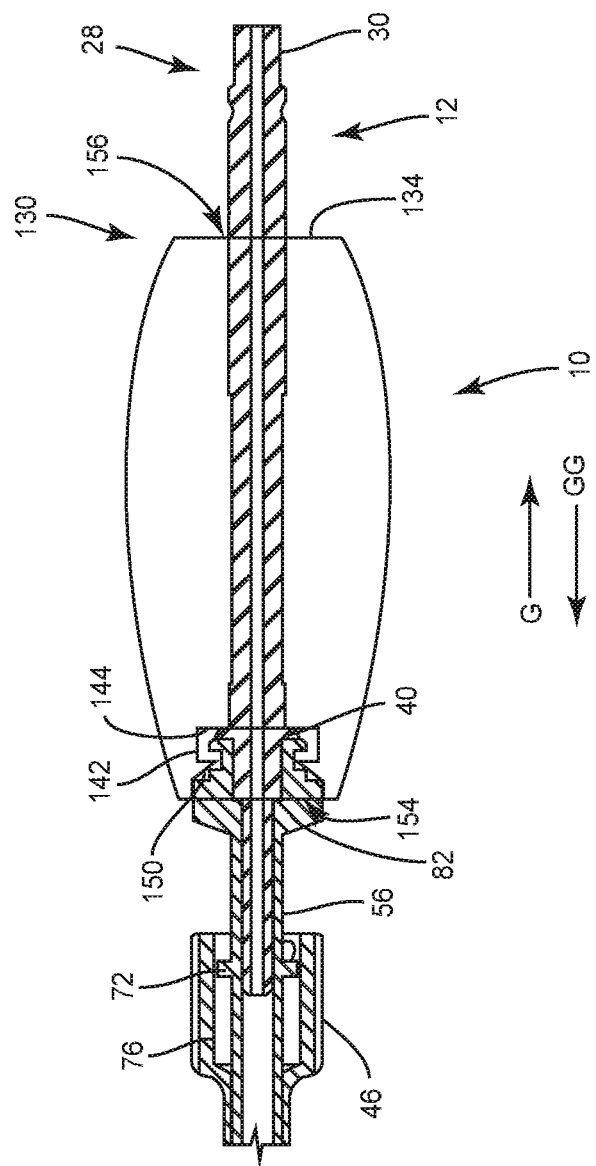
FIG. 8 is a side, cross section view of components of a surgical system in accordance with the principles of the present disclosure.
Figure 9:
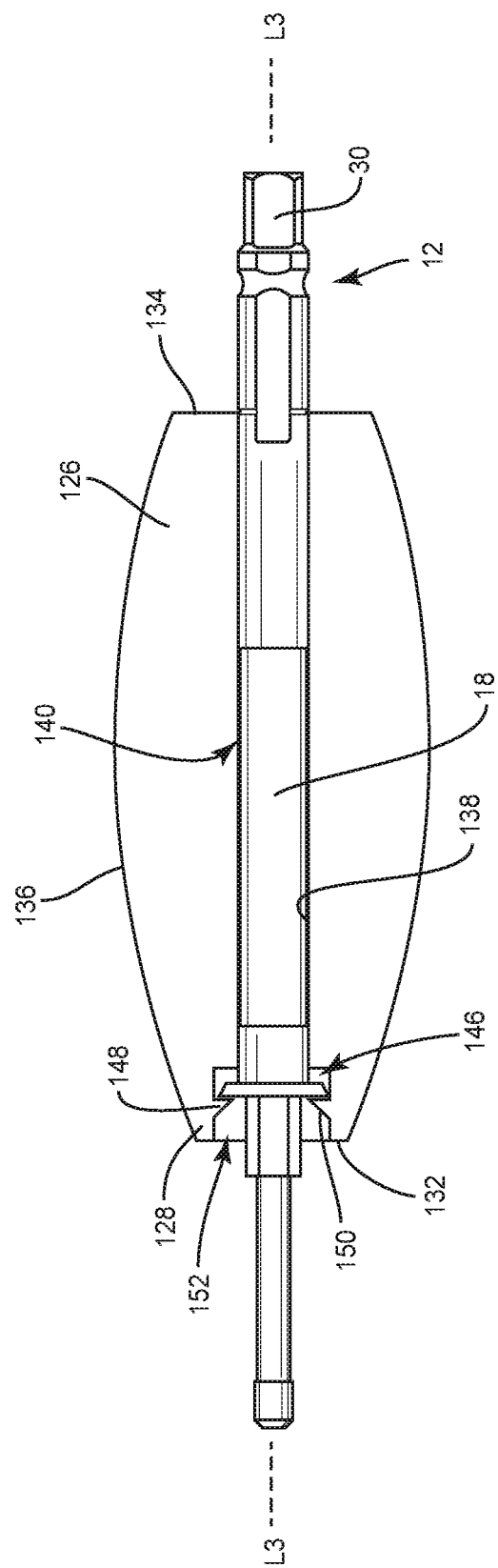
FIG. 9 is a side, cross section view of components of the surgical system shown in FIG. 8.
Figure 10:
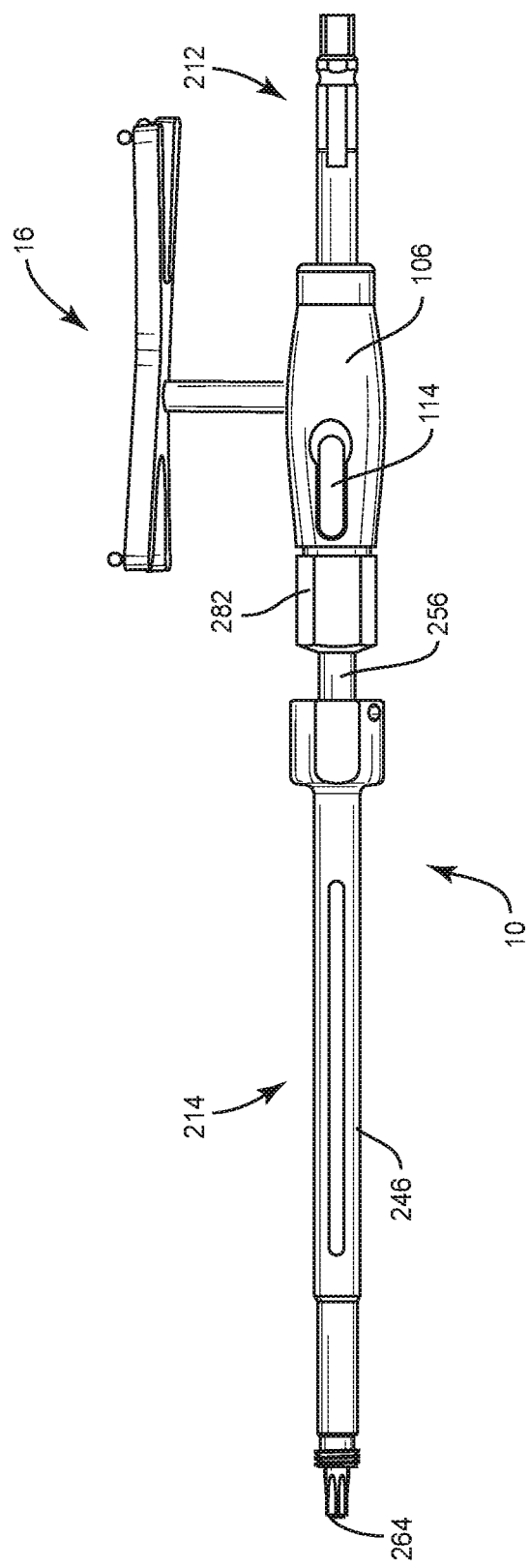
FIG. 10 is a side view of components of one embodiment of a surgical system in accordance with the principles of the present disclosure.
Figure 11:
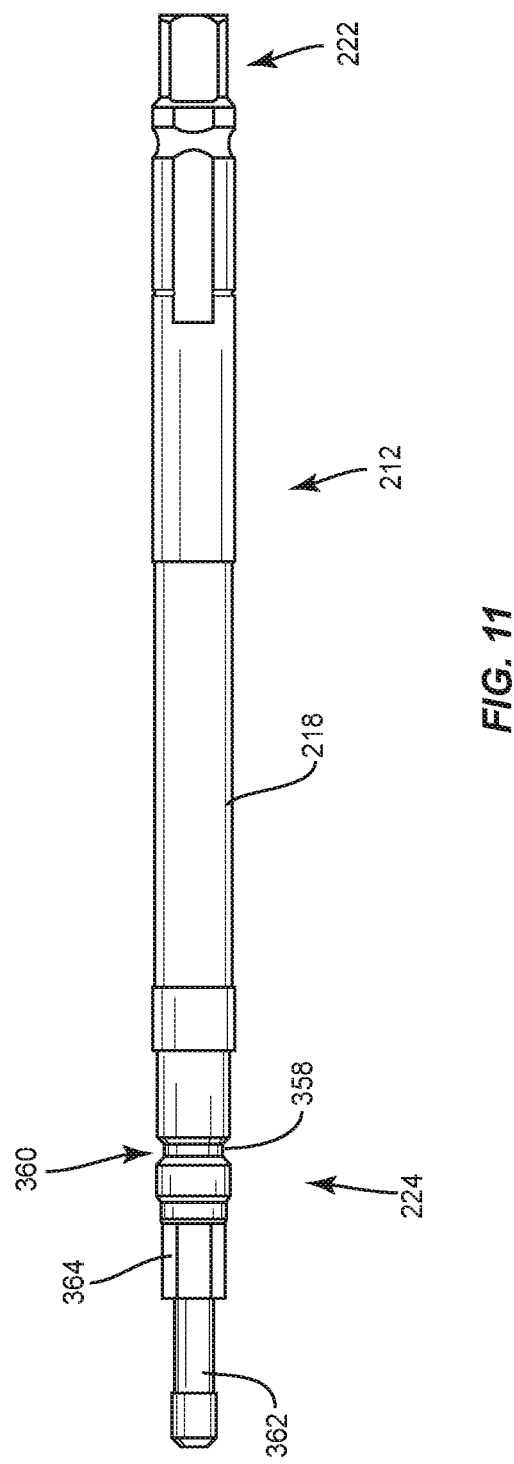
FIG. 11 is a side view of components of the surgical system shown in FIG. 10.

In one embodiment, as shown in FIGS. 8 and 9, surgical system 10 includes a navigation component 126 similar to navigation component 16 that is removably attachable with adaptor 12 and/or driver 14, described herein. Navigation component 126 extends along a longitudinal axis L3 between an end 128 and an opposite end 130, End 128 includes an end surface 132 and end 130 includes an end surface 134. In some embodiments, end surfaces 132, 134 are planar and extend perpendicular to axis L3.

Navigation component 126 includes an inner surface 138 that extends parallel to axis L3 and defines a passageway 140. In some embodiments, passageway 140 has a uniform diameter along the entire length of passageway 140. Navigation component 126 includes opposing transverse surfaces 142, 144 that define a portion of a cavity 146 that is in communication with passageway 140. In some embodiments, cavity 146 has a uniform diameter along the entire length of cavity 146. Navigation component 126 comprises a circumferential flange 148 that includes a surface 150 that defines a portion of a tapered aperture 152, Surface 150 extends transverse to axis L3 to define a ramp, as discussed herein. Navigation component 126 includes an opening 154 that extends through end surface 132 and is in communication with aperture 152 and an opening 156 that extends through end surface 134 and is in communication with passageway 140. In some embodiments, surface 142, surface 144, flange 148 and/or surface 150 may be disposed at alternate orientations, relative to axis L3, such as, for example, transverse, perpendicular and/or other angular orientations such as acute or obtuse, co-axial and/or may be offset or staggered.

Navigation component 126 is connected to adaptor 12 and driver 14, similar to that discussed herein. Adaptor 12 and driver 14 are connected with navigation component 126 by inserting end 22 through opening 154 and translating adaptor 12 and driver 14 relative to navigation component 126 along axis L3, in the direction shown by arrow G in FIG. 8, until flange 40 and/or flange 102 engage flange 148. Adaptor 12 and driver 14 are translated relative to navigation component 126 along axis L3, in the direction shown by arrow G in FIG. 8, such that flange 40 and/or flange 102 slide along the ramp defined by surface 150. Flange 40 and/or flange 102 slide along the ramp defined by surface 150 until flange 40 and flange 102 move from aperture 152 to cavity 146 and flange 148 is disposed in recess 104 of hub 82. In some embodiments, adaptor 12 and driver 14 are coupled to navigation component 126 such that adaptor 12 and navigation component 126 are fixed relative to shaft 56 such that rotation of adaptor 12 or navigation component 126 relative to sleeve 46 about axes L1, L2 also rotates shaft 56 about axes L1, L2. In some embodiments, navigation component 126 can be variously connected with adaptor 12 and/or driver 14, such as, for example, monolithic, integral connection, frictional engagement, threaded engagement, mutual grooves, screws, adhesive, nails, barbs and/or raised element.

In some embodiments, driver 14 may be removed from adaptor 12 while adaptor 12 is connected to navigation component 126, as shown in FIG. 9. Driver 14 is removed from adaptor 12 by translating driver 14 relative to adaptor 12, in the direction shown by arrow GG in FIG. 8, such that flange 102 translates over flange 148 to move flange 102 from cavity 146 to aperture 152. Driver 14 is further translated relative to adaptor 12, in the direction shown by arrow GG in FIG. 8, to completely remove driver 14 from adaptor 12 such that flange 40 remains in cavity 146 after driver 14 has been removed from adaptor 14 to allow navigation component 126 and adaptor 12 to remain attached. In some embodiments, adaptor 12 and navigation component 126 are fixed, as described herein, and concurrently removable from driver 14.

Figure 13:
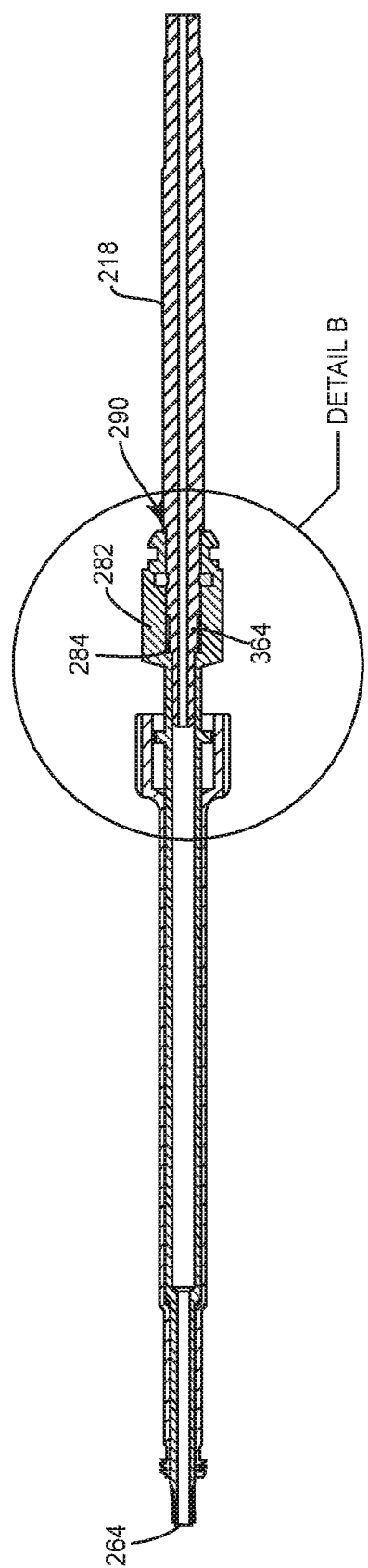
FIG. 13 is a side, cross section view of the components shown in FIG. 10.
Figure 14:
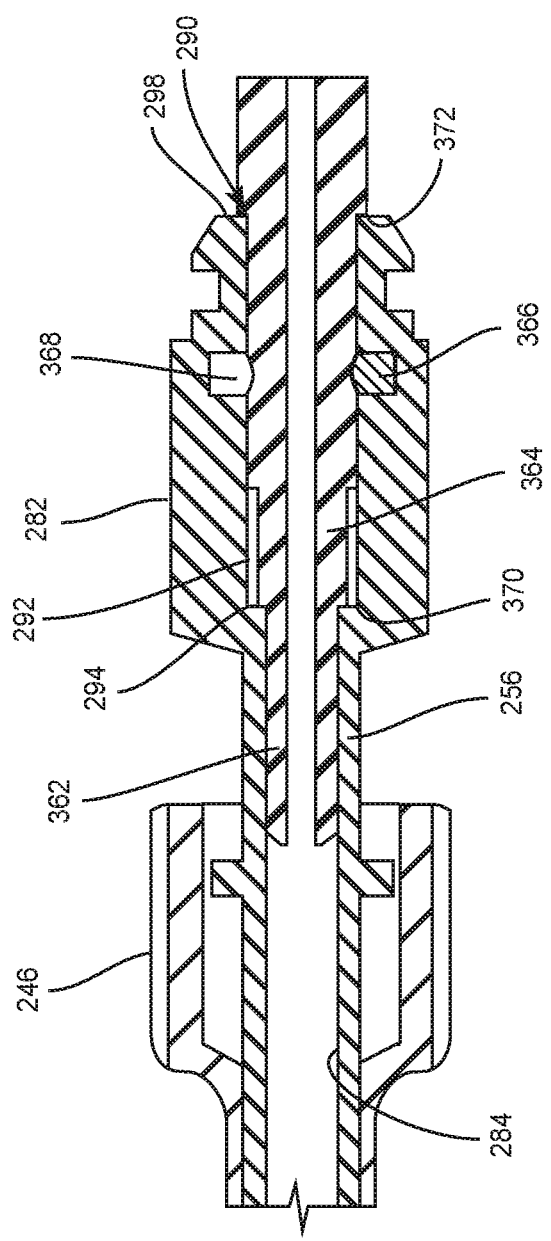
FIG. 14 is an enlarged view of detail B shown in FIG. 13.
Figure 15:
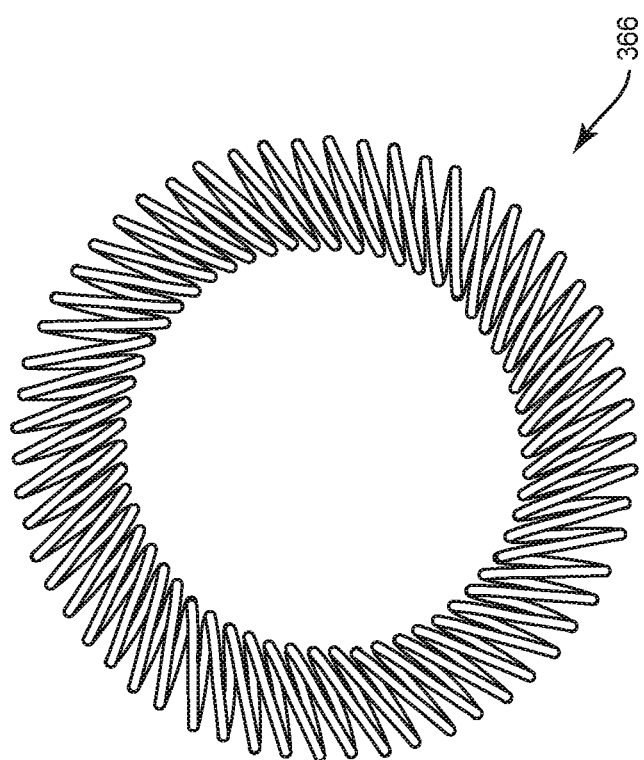
FIG. 15 is a side view of components of the surgical system shown in FIG. 10.

In one embodiment, as shown in FIGS. 10-15, surgical system 10 includes an adaptor 212, similar to adaptor 12 described herein. Adaptor 212 includes an end portion 224, similar to end portion 24 described herein. End portion 224 includes a mating surface 358 configured for engagement with a driver 214, similar to driver 14 described herein, to connect adaptor 212 to driver 214, End portion 224 incudes a circumferential recess 360 defined by mating surface 358, a prong 362, similar to prong 42 described herein, and a section 364, similar to section 44 described herein, positioned between recess 360 and prong 362. Recess 360 is configured for disposal of an elastic member, for example, a spring 366 to releasably connect adaptor 212 with driver 214, as discussed herein. In some embodiments, spring 366 is a coil spring. In some embodiments, spring 366 is a canted coil spring, as shown in FIG. 15.

A hub 282 of driver 214, similar to hub 82 described herein, includes a circumferential notch 368 that extends into an inner surface 284 of hub 282 without extending through an opposite outer surface of hub 282. Notch 368 is configured for disposal of spring 366 to releasably connect adaptor 212 with driver 214.

Adaptor 212 is coupled to driver 214 by inserting prong 362 into an opening 290 of driver 214, similar to opening 90 described herein. Adaptor 212 is translated relative to a shaft 256 of driver 214, similar to shaft 56 described herein, in the direction shown by arrow H in FIG. 12, such that a tip of prong 362 is positioned between hub 282 and a tip 264 of shaft 256, similar to tip 64 described herein, such that a surface 370 of section 364 directly engages a surface 294 of driver 214, and a surface 372 of a shaft 218 of adaptor 212, similar to shaft 18 described herein, directly engages end surface 298 of hub 282, and spring 366 is positioned in recess 360 and notch 368, as shown in FIGS. 13 and 14.

Figure 12:
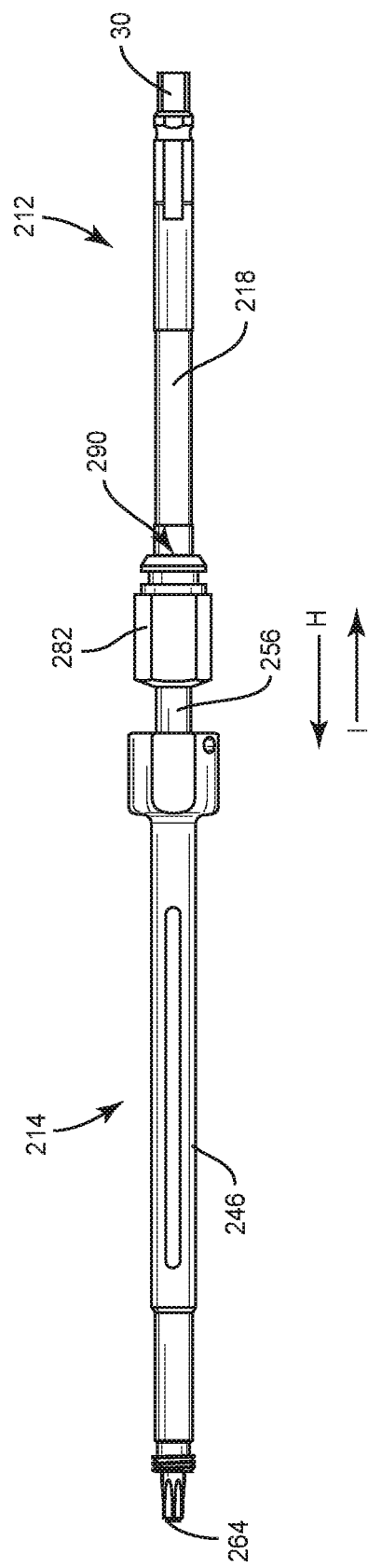
FIG. 12 is a side view of components of the surgical system shown in FIG. 10.

In some embodiments, spring 366 is a canted spring configured to allow adaptor 212 to translate relative to shaft 256 in one direction, such as, for example, the direction shown by arrow H in FIG. 12, and to prevent adaptor 212 from translating relative to shaft 256 in an opposite direction, such as, for example, the direction shown by arrow I in FIG. 12. In some embodiments, spring 366 is configured such that a force is required to overcome a bias of spring 366 to remove spring 366 from notch 368. For example, a force is required to compress spring 366 such that spring 366 has a diameter that is less than or equal to a diameter of an aperture 292 of driver 214, similar to aperture 92 described herein. Once spring 366 is compressed, adaptor 212 is translated relative to shaft 256, in the direction shown by arrow I in FIG. 12, until spring 366 is removed from notch 368. After spring 366 is removed from notch 368, adaptor 212 can translate relative to shaft 256, in the direction shown by arrow I in FIG. 12, to completely remove adaptor 212 from driver 214. In some embodiments, surface 370 and/or surface 372 may be disposed at alternate orientations, relative to a longitudinal axis of adaptor 212, such as, for example, transverse, perpendicular and/or other angular orientations such as acute or obtuse, co-axial and/or may be offset or staggered.

In some embodiments, adaptor 212 is coupled to driver 214 such that adaptor 212 is fixed relative to shaft 256 such that rotation of adaptor 212 relative to a sleeve 246 of driver 214, similar to sleeve 46 described herein, also rotates shaft 256 relative to sleeve 246. For example, in some embodiments, section 364 has a polygonal cross sectional configuration, such as, for example, a hexagonal cross sectional configuration and aperture 292 has a polygonal cross sectional configuration, such as, for example, a hexagonal cross sectional configuration that corresponds to the cross sectional configuration of section 364 such that an outer surface of section 364 directly engages surface 284 within aperture 292 to prevent adaptor 212 from rotating relative to shaft 256.

Figure 16:
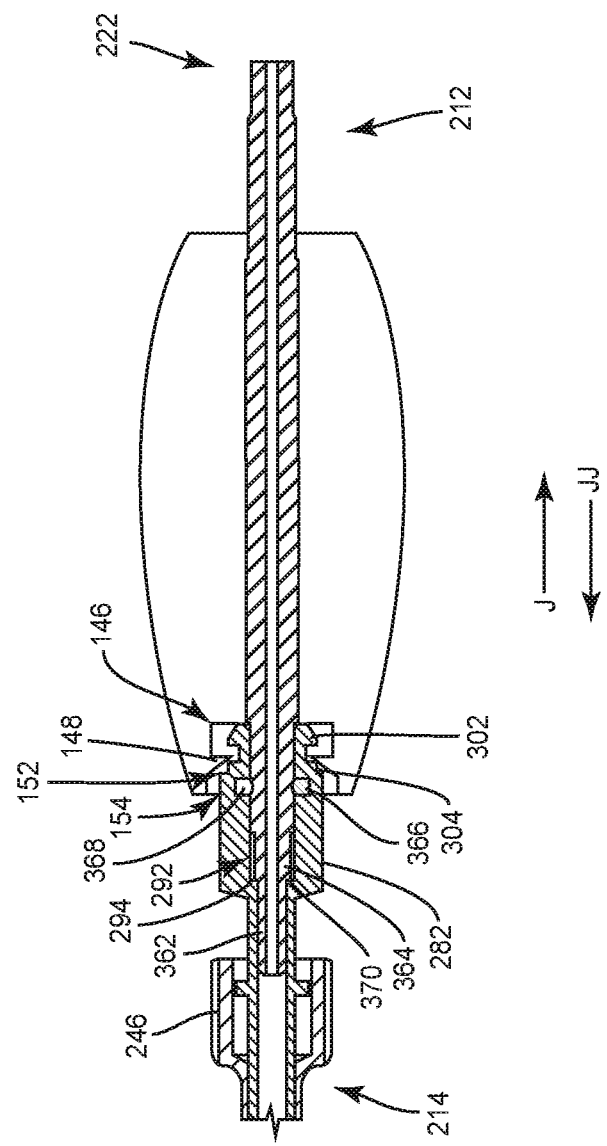
FIG. 16 is a side, cross section view of components of a surgical system in accordance with the principles of the present disclosure.
Figure 16A:
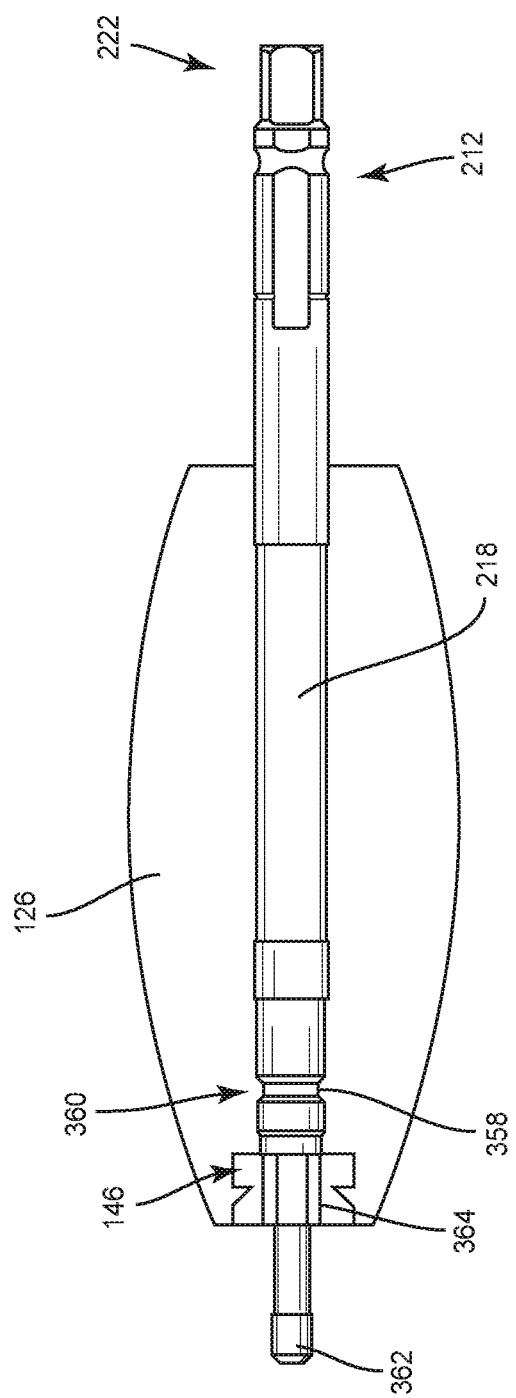
FIG. 16A is a side, cross section view of components of the surgical system shown in FIG. 16.
Figure 17:
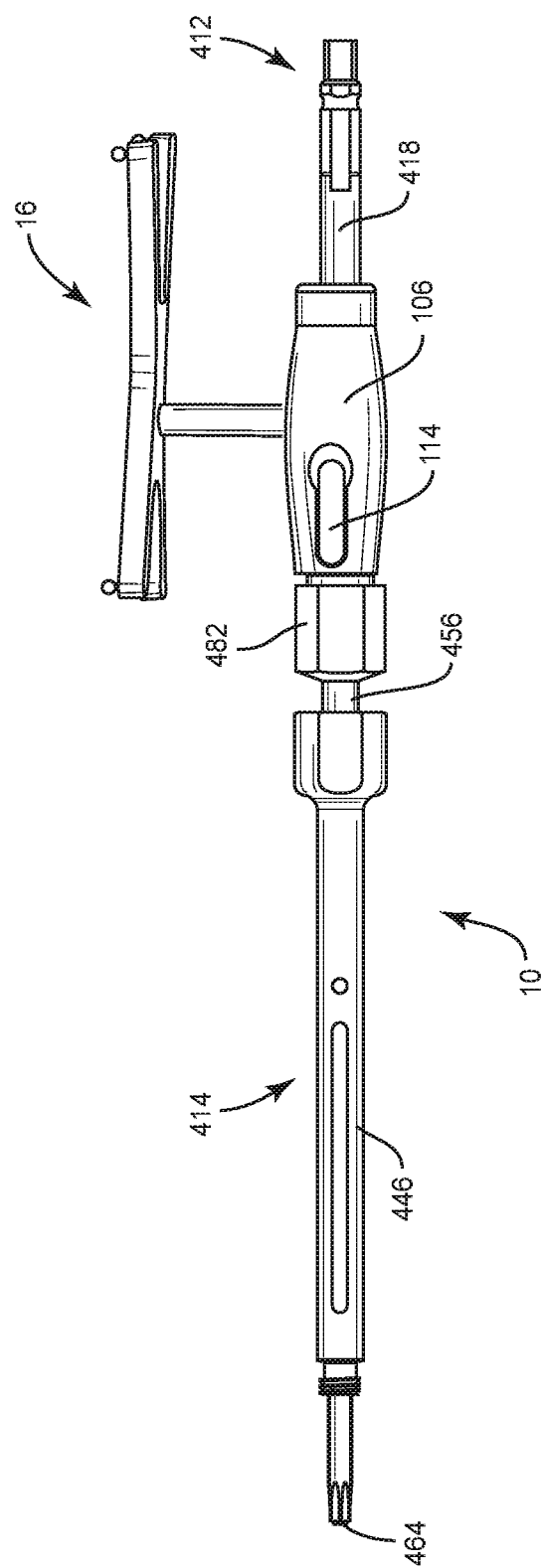
FIG. 17 is a side view of components of one embodiment of a surgical system in accordance with the principles of the present disclosure.
Figure 18:
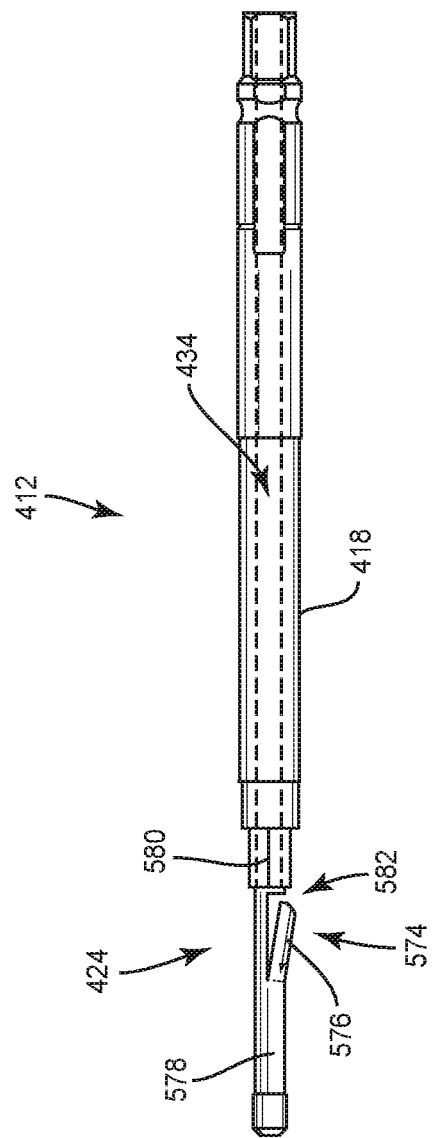
FIG. 18 is a side view of components of the surgical system shown in FIG. 17.

In one embodiment, as shown in FIGS. 16 and 16A, navigation component 126, described herein, is removably attachable with adaptor 212 and driver 214. Adaptor 212 is coupled to driver 214 by inserting prong 362 into opening 290. Adaptor 212 is translated relative to shaft 256, in the direction shown by arrow H in FIG. 12, such that a tip of prong 362 is positioned between hub 282 and tip 264, surface 370 of section 364 directly engages surface 294, surface 372 of shaft 218 directly engages end surface 298 of hub 282, and spring 366 is positioned in recess 360 and notch 368, as shown in FIG. 14. Navigation component 126 is connected to adaptor 212 and driver 214 inserting an end 222 of adaptor 212, similar to end 22 described herein, through opening 154 and translating adaptor 212 and driver 214 relative to navigation component 126, in the direction shown by arrow J in FIG. 16, until a flange 302 of driver 214, similar to flange 102 described herein, engages flange 148. Adaptor 212 and driver 214 are translated relative to navigation component 126, in the direction shown by arrow J in FIG. 16, such that flange 302 slides along the ramp defined by surface 150. Flange 302 slides along the ramp defined by surface 150 until flange 302 moves from aperture 152 to cavity 146 and flange 148 is disposed in a recess 304 of hub 282, similar to recess 104 described herein, as shown in FIG. 16.

In some embodiments, driver 214 may be removed from adaptor 212 while adaptor 212 is connected to navigation component 126, as shown in FIG. 16A. Driver 214 is removed from adaptor 212 by translating driver 214 relative to adaptor 212, in the direction shown by arrow JJ in FIG. 16, such that flange 302 translates over flange 148 to move flange 302 from cavity 146 to aperture 152, Driver 214 is further translated relative to adaptor 212, in the direction shown by arrow JJ in FIG. 16, to completely remove driver 214 from adaptor 212 to allow navigation component 126 and adaptor 212 to remain attached, as shown in FIG. 16A. In some embodiments, adaptor 212 and navigation component 126 are fixed, as described herein, and concurrently removable from driver 214. In some embodiments, driver 214 and navigation component 126 are fixed, as described herein, and concurrently removable from adaptor 212. For example, spring 366 is compressed, as described herein, and adaptor 212 is translated relative to shaft 256, in the direction shown by arrow I in FIG. 12, until spring 366 is removed from notch 368. After spring 366 is removed from notch 368, adaptor 212 can translate relative to shaft 256, in the direction shown by arrow I in FIG. 12, to completely remove adaptor 212 from driver 214 and navigation component 126.

In one embodiment, shown in FIGS. 17-21, surgical system 10 includes an adaptor 412, similar to adaptors 12, 212 described herein. Adaptor 412 includes an end portion 424, similar to end portions 24, 224 described herein. End portion 424 includes a mating surface 574 that includes an outwardly biased element, such as, for example, an outwardly spring biased finger 576. End portion 424 comprises a prong 578 and includes finger 576 and a section 580 positioned between prong 578 and a shaft 418 of adaptor 412, similar to shaft 18 described herein. Prong 578 includes an aperture 582 between section 580 and finger 576 configured to allow finger 576 to deflect relative to prong 578. Aperture 582 is in communication with a passageway 434 of adaptor 412, similar to passageway 34 described herein. In some embodiments, prong 578 and/or section 580 may have various cross section configurations, such as, for example, circular, oval, oblong, triangular, rectangular, square, polygonal, irregular, uniform, non-uniform, variable, tubular and/or tapered.

Driver 414 includes a surface 484 that defines a channel 486, similar to channel 86 of driver 14 described herein. Channel 486 includes a tapered portion 584 defined by a section 586 of surface 484 and a section 588 of surface 484. Section 588 extends transverse to section 586. Portion 584 is configured for disposal of finger 576, as discussed herein. In some embodiments, section 586 and/or section 588 may be disposed at alternate orientations, relative to a longitudinal axis defined by driver 414, such as, for example, transverse, perpendicular and/or other angular orientations such as acute or obtuse, co-axial and/or may be offset or staggered.

Figure 20:
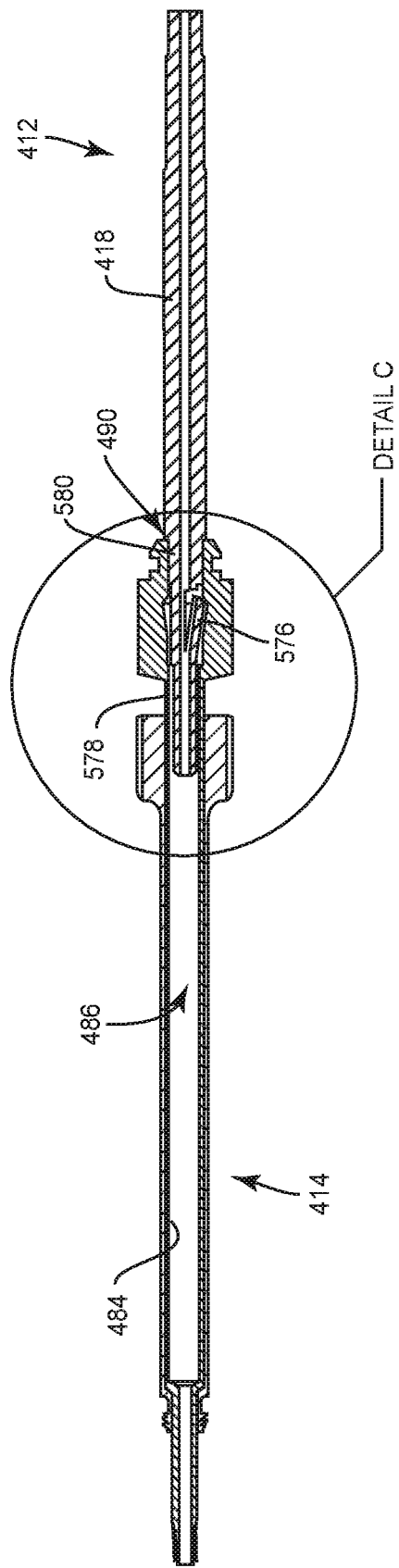
FIG. 20 is a side, cross section view of components of the surgical system shown in FIG. 17.
Figure 21:
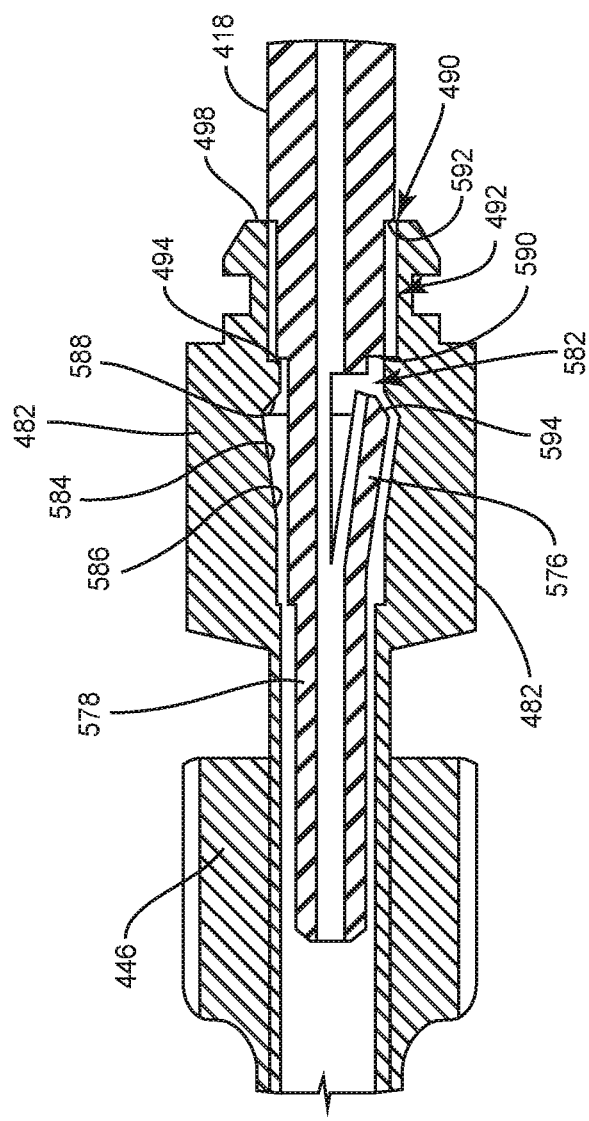
FIG. 21 is an enlarged view of detail C shown in FIG. 20.

Adaptor 412 is coupled to driver 414 by inserting prong 578 into an opening 490 of driver 414, similar to openings 90, 290 described herein. Adaptor 412 is translated relative to a shaft 456 of driver 414, similar to shafts 56, 256 described herein, in the direction shown by arrow K in FIG. 19, such that a tip of prong 578 is positioned between a hub 482 of driver 414, similar to hubs 82, 282 described herein, and a tip 464 of driver 414, similar to tips 64, 264 described herein, such that finger 576 directly engages section 586 and/or section 588, and a transverse surface 590 of section 580 directly engages a surface 494 of driver 414, similar to surface 94 described herein, and a transverse surface 592 of shaft 418 directly engages an end surface 498 of hub 482, similar to end surfaces 98, 298 described herein, as shown in FIGS. 20 and 21. In some embodiments, navigation component 126 is removably attachable with adaptor 412 and driver 414, similar to that described herein with regard to adaptor 212 and driver 214. In some embodiments, adaptor 412 and navigation component 126 are fixed, as described herein, and concurrently removable from driver 414.

In some embodiments, adaptor 412 is coupled to driver 414 such that adaptor 412 is fixed relative to shaft 456 such that rotation of adaptor 412 relative to a sleeve 446 of driver 414, similar to sleeves 46, 246 described herein, also rotates shaft 456 relative to sleeve 446. For example, in some embodiments, section 580 has a polygonal cross sectional configuration, such as, for example, a hexagonal cross sectional configuration and an aperture 492 of driver 414, similar to apertures 92, 292 described herein, has a polygonal cross sectional configuration, such as, for example, a hexagonal cross sectional configuration that corresponds to the cross sectional configuration of section 580 such that an outer surface of section 580 directly engages surface 484 within aperture 492 to prevent adaptor 412 from rotating relative to shaft 456.

Figure 19:
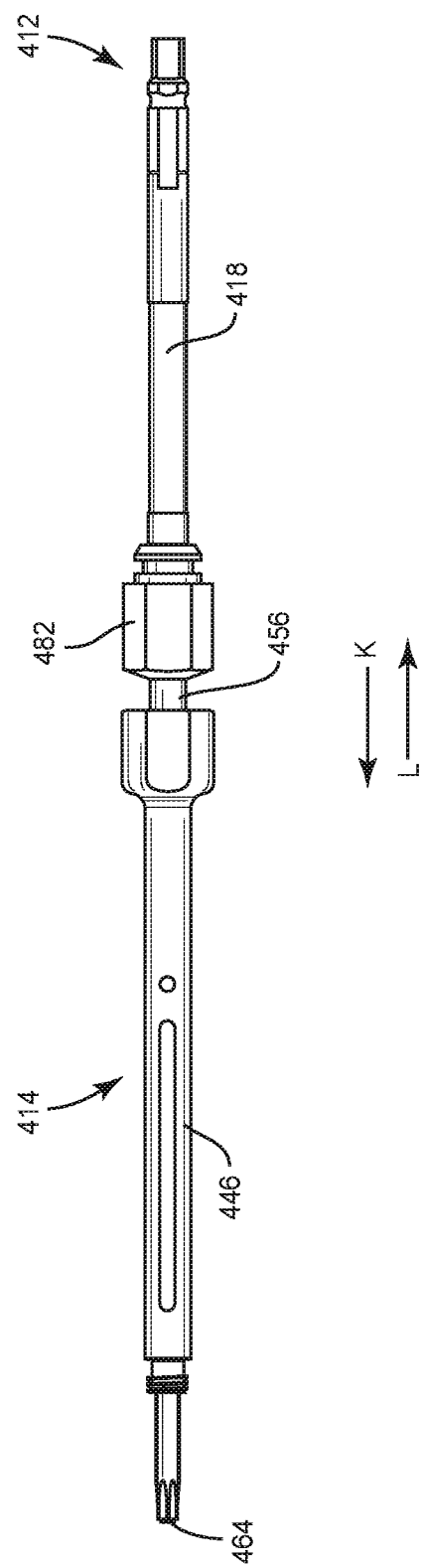
FIG. 19 is a side view of components of the surgical system shown in FIG. 17.

In some embodiments, adaptor 412 can be removed from driver 414 by translating adaptor 412 relative to driver 414, in the direction shown by arrow L in FIG. 19. Section 588 defines a ramp configured to engage a surface 594 of finger 576 such that surface 594 slides along section 588. Adaptor 412 can be translated relative to driver 414, in the direction shown by arrow L in FIG. 19, until surface 590 is spaced apart from surface 494, surface 592 is spaced apart from surface 498, and finger 576 is removed from channel 486 to completely remove adaptor 412 from driver 414. In some embodiments, driver 414 and navigation component 126 are fixed, as described herein, and removable from adaptor 412, as described herein.

Figure 22:
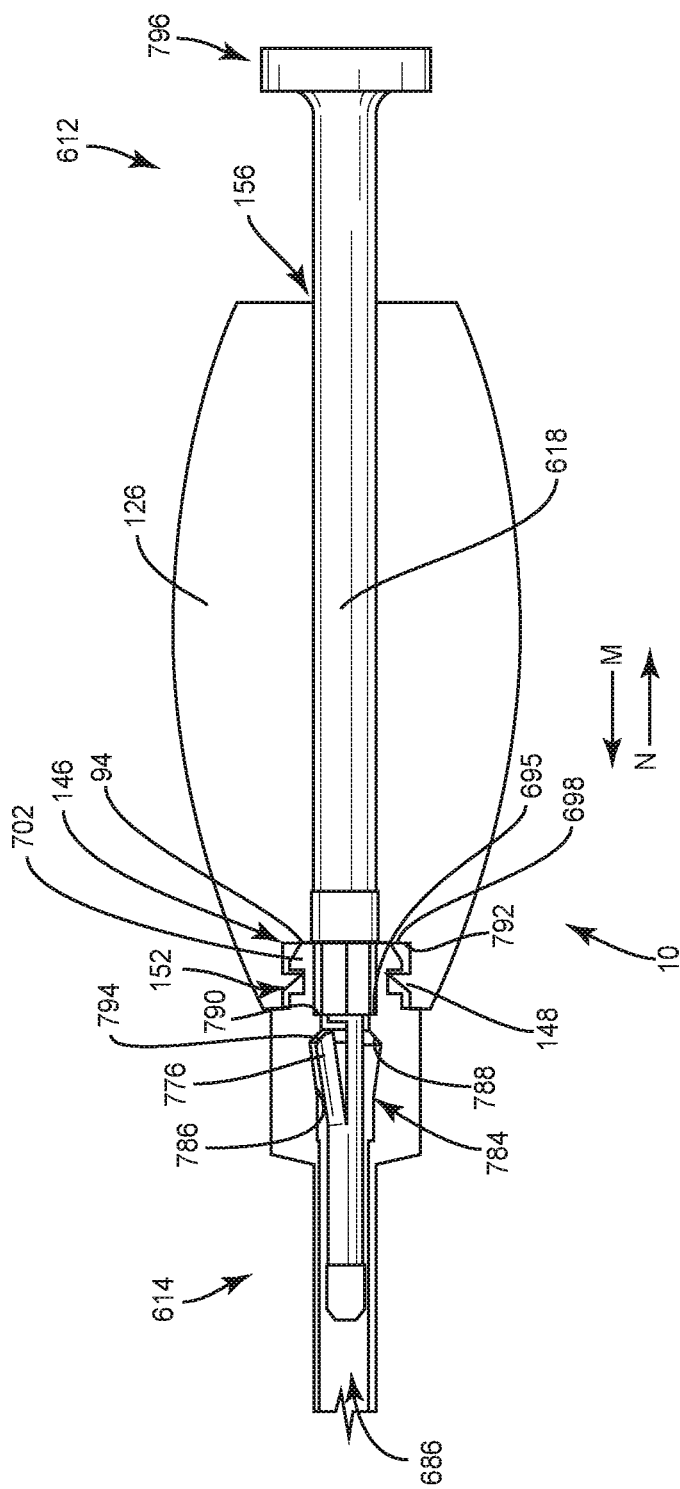
FIG. 22 is a side, cross section view of components of the surgical system shown in FIG. 17.
Figure 23:
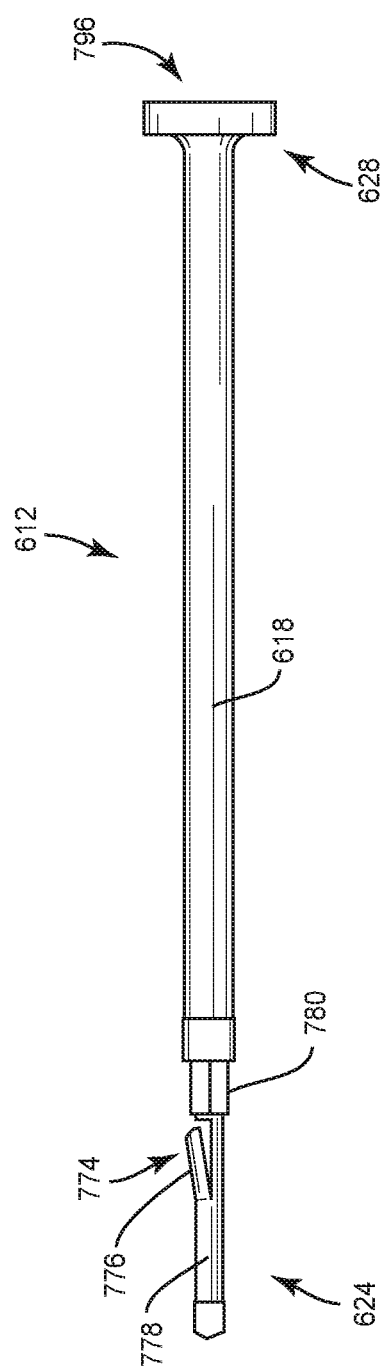
FIG. 23 is a side view of components of one embodiment of a surgical system in accordance with the principles of the present disclosure.
Figure 24:
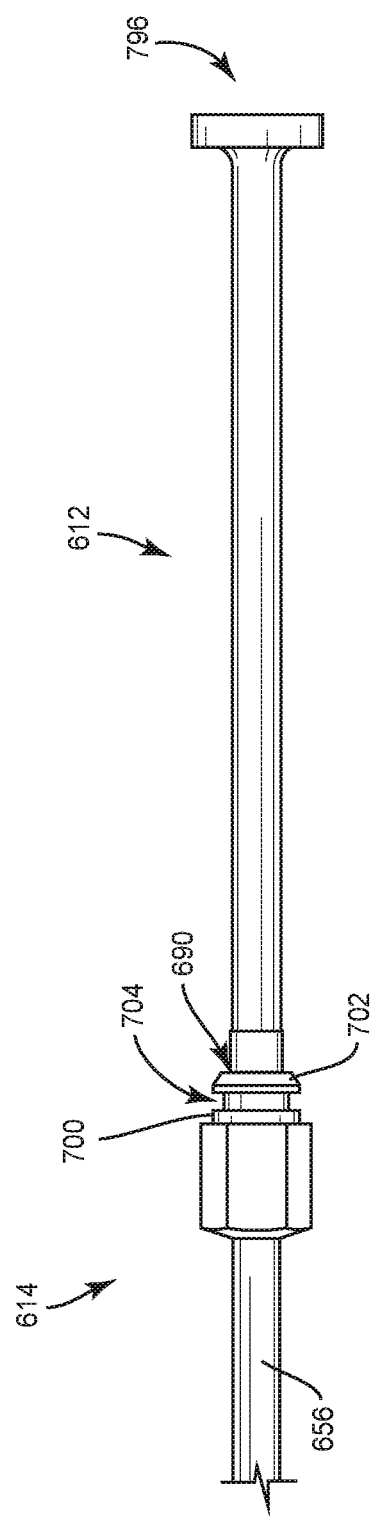
FIG. 24 is a side view of components of one embodiment of a surgical system in accordance with the principles of the present disclosure.

In one embodiment, as shown in FIGS. 22-24, surgical system 10 includes a surgical instrument, such as, for example, an inserter 614 and navigation component 126 being fixed, similar to the attachment of driver 414 and navigation component 126 described herein, and removable from adaptor 412, as described herein. For example, adaptor 412 is removed from inserter 614/component 126 and an alternate surgical instrument, such as, for example, a mallet attachment 612 is attached to inserter 614 and navigation component 126, similar to adaptor 412 described herein.

Mallet attachment 612 includes an end portion 624 having a mating surface 774 that includes a finger 776, similar to finger 576 described herein. End portion 624 comprises finger 776, a prong 778, similar to prong 578 described herein, and a section 780, similar to section 580 described herein. Mallet attachment 612 includes an end portion 628 that comprises a striking portion 796. Striking portion 796 is configured to be struck by an instrument or tool, such as, for example, a mallet. Inserter 614 includes a channel 686. Channel 686 includes tapered portion 784, similar to portion 584 described herein. Portion 784 is defined by a section 786, similar to section 586 described herein and a section 788, similar to section 588 described herein.

Prong 778 of mallet attachment 612 is inserted into opening 156 of navigation component 126. Mallet attachment 612 is translated relative to navigation component 126, in the direction shown by arrow N in FIG. 22, until a flange 702 of inserter 614 engages flange 148. Mallet attachment 612 is translated relative to navigation component 126, in the direction shown by arrow N in FIG. 22, such that flange 702 slides along the ramp defined by surface 150. Flange 702 slides along the ramp defined by surface 150 until flange 702 moves from aperture 152 to cavity 146 and flange 148 is disposed in a recess 704 of hub 682.

Mallet attachment 612 is coupled to inserter 614 by inserting prong 778 into an opening 690 of inserter 614, similar to that described herein. Mallet attachment 612 is translated relative to a shaft 656 of inserter 614, similar to that described herein, in the direction shown by arrow M in FIG. 22, such that the tip of prong 778 is positioned between a hub 682 of inserter 614, similar to that described herein, and a tip of shaft 656. Finger 776 directly engages section 786 and/or section 788 and a transverse surface 790 directly engages a surface 695 of inserter 614. A transverse surface 792 of a shaft 618 directly engages an end surface 698 of hub 682.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument adaptor comprising:
   a member removably attachable with a surgical instrument, the member comprising a first mating surface and a second mating surface, the second mating surface being connectable with an actuator, the member including an inner surface defining a passageway, the passageway extending continuously along an entire length of the member; and
   an image guide attachable with the member and oriented relative to a sensor to communicate a signal representative of a position of the surgical instrument,
   wherein the first mating surface includes a flange engageable with a lock of the image guide to fix the member with the image guide, the flange defining a maximum diameter of the member.

2. A surgical instrument adaptor as recited in claim 1, wherein the image guide includes an inner surface that defines a cavity configured for disposal of the member.

3. A surgical instrument adaptor as recited in claim 1, wherein the image guide includes a tubular body that defines an axial cavity configured for disposal of the member.

4. A surgical instrument adaptor as recited in claim 1, wherein the lock includes a pair of tabs, the tabs being rotatable relative to a body of the image guide.

5. A surgical instrument adaptor as recited in claim 1, wherein the image guide includes an emitter configured to generate a signal representative of the position of the surgical instrument.

6. A surgical instrument adaptor as recited in claim 1, wherein the flange is a circumferential flange.

7. A surgical instrument adaptor as recited in claim 1, wherein the lock includes a pair of tabs, the tabs being rotatable relative to a body of the image guide between a first orientation in which the tabs engage the flange and a second orientation in which the tabs are spaced apart from the flange.

8. A surgical instrument adaptor as recited in claim 1, wherein the member includes a wall including the inner surface and an opposite outer surface, the wall being free of any openings extending through the inner and outer surfaces.

9. A surgical instrument adaptor as recited in claim 1, wherein the member comprises a prong, the flange being positioned between the prong and the second mating surface.

10. A surgical instrument adaptor as recited in claim 1, wherein the member comprises a prong, the prong having a first portion and a second portion, the second portion having a diameter greater than a diameter of the first portion, the first portion being positioned between the second portion and the flange.

11. A surgical instrument adaptor as recited in claim 1, wherein the member comprises a prong, the flange being positioned between the prong and the second mating surface, the prong having a polygonal cross-sectional configuration.

12. A surgical instrument adaptor as recited in claim 1, wherein the second mating surface includes a drive bit.

13. A surgical instrument adaptor as recited in claim 1, wherein the actuator includes a ratchet handle.

14. A surgical instrument adaptor as recited in claim 1, wherein the actuator includes a powered drill.

15. A surgical system comprising:
    a surgical instrument including a distal end and a proximal mating surface;
    an adaptor being removably attachable with the surgical instrument, the adaptor comprising a first mating surface and a second mating surface, the adaptor including an inner surface defining a passageway, the passageway extending continuously along an entire length of the adaptor;
    an actuator connected with the second mating surface; and
    an image guide attached with the adaptor and oriented relative to a sensor to communicate a signal representative of a position of the surgical instrument,
    wherein the first mating surface includes a flange engageable with a lock of the image guide to fix the adaptor with the image guide, the flange defining a maximum diameter of the adaptor.

16. A surgical instrument adaptor as recited in claim 15, wherein the lock is engageable with the flange such that the adaptor and the image guide are fixed and concurrently removable from the surgical instrument.

17. A surgical instrument adaptor as recited in claim 15, wherein the lock includes a pair of tabs, the tabs being rotatable relative to a body of the image guide between a first orientation in which the tabs engage the flange and a second orientation in which the tabs are spaced apart from the flange.

18. A surgical instrument adaptor as recited in claim 15, wherein the surgical instrument and the image guide are fixed and concurrently removable from the adaptor such that an alternative surgical instrument is removably attachable with the first mating surface.

19. A surgical system comprising:
    a surgical instrument including a distal end and a proximal mating surface;
    an adaptor being removably attachable with the surgical instrument, the adaptor comprising a first mating surface and a second mating surface, the adaptor including an inner surface defining a passageway, the passageway extending continuously along an entire length of the adaptor;
    an actuator connected with the second mating surface;
    an image guide including a tubular body that defines an axial cavity configured for disposal of the adaptor and an emitter oriented relative to a sensor to communicate a signal representative of a position of the surgical instrument; and
    an alternative surgical instrument removably attachable with the flange,
    wherein the first mating surface includes a flange engageable with a lock of the image guide to fix the adaptor with the image guide, the flange defining a maximum diameter of the adaptor.

20. A surgical system as recited in claim 19, wherein the surgical instrument includes an inserter and the alternative surgical instrument includes a mallet.

\* \* \* \* \*